(12) United States Patent
Kim et al.

(10) Patent No.: US 9,296,751 B1
(45) Date of Patent: Mar. 29, 2016

(54) INDOLIZINO[3,2-C]QUINOLINE DERIVATIVES, PHARMACEUTICALLY ACCEPTABLE SALT THEREOF, PREPARATION METHOD THEREOF AND PHARMACEUTICAL COMPOSITION FOR TREATMENT OF CYSTIC FIBROSIS CONTAINING THE SAME AS ACTIVE INGREDIENT

(71) Applicant: INDUSTRY-ACADEMIC COOPERATION FOUNDATION, YONSEI UNIVERSITY, Seoul (KR)

(72) Inventors: Ikyon Kim, Incheon (KR); Wan Namkung, Incheon (KR); Jonghyuk Sung, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/884,179

(22) Filed: Oct. 15, 2015

(30) Foreign Application Priority Data

Oct. 16, 2014 (KR) ........................ 10-2014-0139609

(51) Int. Cl.
*A61K 31/4745* (2006.01)
*C07D 471/06* (2006.01)
*C07D 471/14* (2006.01)

(52) U.S. Cl.
CPC .................................. *C07D 471/14* (2013.01)

(58) Field of Classification Search
USPC ............................................ 514/285; 546/70
See application file for complete search history.

(56) References Cited

U.S. PATENT DOCUMENTS

| 5,155,255 | A | 10/1992 | Mazzuchelli et al. |
| 7,999,113 | B2 | 8/2011 | Hadida-Ruah et al. |
| 8,314,239 | B2 | 11/2012 | Binch et al. |
| 8,410,321 | B2 | 4/2013 | Holtzapple et al. |
| 8,586,615 | B2 | 11/2013 | Hadida-Ruah et al. |
| 8,614,325 | B2 | 12/2013 | Yang et al. |
| 2011/0257233 | A1 | 10/2011 | Cosford et al. |

FOREIGN PATENT DOCUMENTS

WO 92/07856 5/1992

OTHER PUBLICATIONS

Park, S. et al.: When indolizine meets quinoline: diversity-oriented synthesis of new polyheterocycles and their optical properties. ACS comb. sci., vol. 17, pp. 459-469, 2015.*

* cited by examiner

*Primary Examiner* — Charanjit Aulakh
(74) *Attorney, Agent, or Firm* — Duane Morris LLP; J. Rodman Steele, Jr.; Gregory M. Lefkowitz

(57) ABSTRACT

Provided are an indolizino[3,2-c]quinoline derivative, pharmaceutically acceptable salt thereof, and a method for preparing the same. The indolizino[3,2-c]quinoline derivative, pharmaceutically acceptable salt thereof may function as an agonist of cystic fibrosis conductance transmembrane regulator, and thus may be useful for an agent for preventing or treating diseases caused by degradation of activity of cystic fibrosis conductance transmembrane regulator and for a pharmaceutical composition for stimulating proliferation of stem cells.

15 Claims, 4 Drawing Sheets

INDOLIZINO[3,2-C]QUINOLINE DERIVATIVES, PHARMACEUTICALLY ACCEPTABLE SALT THEREOF, PREPARATION METHOD THEREOF AND PHARMACEUTICAL COMPOSITION FOR TREATMENT OF CYSTIC FIBROSIS CONTAINING THE SAME AS ACTIVE INGREDIENT

CROSS-REFERENCE TO RELATED APPLICATIONS

This application claims priority under 35 U.S.C. §119 to Korean Patent Application No. 10-2014-0139609 filed on Oct. 16, 2014 in the Korean Intellectual Property Office, the disclosure of which is incorporated herein by reference in its entirety.

TECHNICAL FIELD

The following disclosure relates to an indolizino[3,2-c] quinoline derivative, pharmaceutically acceptable salt thereof, method for preparing the same and a pharmaceutical composition for preventing or treating cystic fibrosis containing the same as an active ingredient.

BACKGROUND

Heterocyclic compounds are regarded as one of the most important compounds in various fields, including material chemistry as well as biochemistry and pharmaceutical chemistry. Particularly, in the field of pharmaceutical chemistry, aromatic heterocyclic compounds have been used as key skeletons. Among such heterocyclic compounds, those having a 5,6-heteroaromatic cycle pattern are reported to provide biological activities, such as antibacterial, antiviral and anticancer activities. They are also reported to provide various pharmacological functions depending on the substitution pattern around an aromatic ring.

A cystic fibrosis conductance transmembrane regulator (CFTR) is a kind of carriers controlling the transport of anions, is expressed by various cell types including absorptive and secretory epithelial cells, and functions to control other ion channels and activity of protein as well as the flow of anions passing through a membrane. CTFR-mediated diseases include chronic obstructive pulmonary disease (COPD), dry eye syndrome or Sjogren's syndrome in addition to cystic fibrosis.

Vertex Pharmaceuticals, Inc. have reported modifiers for cystic fibrosis conductance transmembrane regulator having various structures through US Patent Application No. 2011-0257233, U.S. Pat. No. 7,999,113, U.S. Pat. No. 8,314,239, U.S. Pat. No. 8,410,321, U.S. Pat. No. 8,586,615, U.S. Pat. No. 8,614,325, or the like. However, the structures reported in the above patent documents are different from the structure of indolizino[3,2-c]quinoline.

Meanwhile, U.S. Pat. No. 5,155,255 discloses a method for preparing 8-methyl-7-(1-oxopropyl)indolizino[1,2-b]quinoline-9(11H)-one and International Patent Publication No. WO1992/007856 discloses the features of an indolizino[1,2-b]quinolinone compound, which merely shows pharmaceutical activity to viral infections due to the above-mentioned structural difference. Thus, there is no report about the compounds having an indolizino[3,2-c]quinoline skeleton disclosed herein.

SUMMARY

An embodiment of the present disclosure is directed to providing an indolizino[3,2-c]quinoline derivative or pharmaceutically acceptable salt thereof.

Another embodiment of the present disclosure is directed to providing a method for preparing the indolizino[3,2-c] quinoline derivative or pharmaceutically acceptable salt thereof.

Still another embodiment of the present disclosure is directed to providing a modifier of cystic fibrosis conductance transmembrane regulator, including the indolizino[3,2-c] quinoline derivative or pharmaceutically acceptable salt thereof as an active ingredient.

Still another embodiment of the present disclosure is directed to providing a pharmaceutical composition for preventing or treating diseases caused by degradation of activity of cystic fibrosis conductance transmembrane regulator, including the indolizino[3,2-c]quinoline derivative or pharmaceutically acceptable salt thereof as an active ingredient.

Yet another embodiment of the present disclosure is directed to providing a pharmaceutical composition for stimulating stem cell proliferation, including the indolizino [3,2-c]quinoline derivative or pharmaceutically acceptable salt thereof as an active ingredient.

To solve the above-mentioned problems, in one aspect, there is provided an indolizino[3,2-c]quinoline derivative represented by the following Chemical Formula 1 or pharmaceutically acceptable salt thereof:

[Chemical Formula 1]

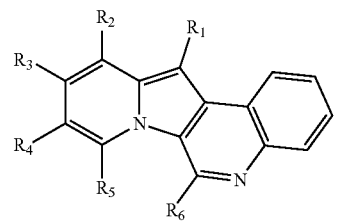

In Chemical Formula 1, $R_1$, $R_2$, $R_3$, $R_4$ and $R_5$ are the same or different, and each independently represents H, F, Cl, Br, I, a C1-C6 alkyl, C1-C6 alkoxy, $COOR_7$, aryl and a heteroaryl;

$R_6$ is selected from a C1-C6 alkyl, aryl and a heteroaryl; and $R_7$ is H or a C1-C6 alkyl, wherein any 1-3 carbon atoms of the aryl and heteroaryl are linked to a substituent that is the same or different and is independently selected from H, F, Cl, Br, I, nitro, a C1-C6 alkyl and C1-C6 alkoxy.

In another aspect, there is provided a method for preparing the indolizino[3,2-c]quinoline derivative represented by Chemical Formula 1. According to the method, the indolizino [3,2-c]quinoline derivative may be obtained by reacting a compound represented by the following Chemical Formula 2 with an aldehyde compound in the presence of a catalyst:

[Chemical Formula 1]

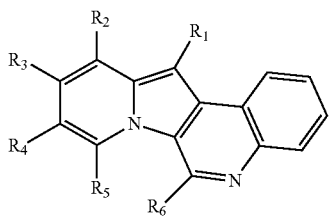

[Chemical Formula 2]

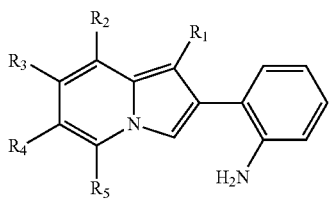

In Chemical Formula 1 or Chemical Formula 2, $R_1$, $R_2$, $R_3$, $R_4$ and $R_5$ are the same or different, and each independently represents H, F, Cl, Br, I, a C1-C6 alkyl, C1-C6 alkoxy, $COOR_7$, aryl and a heteroaryl;

$R_6$ is selected from a C1-C6 alkyl, aryl and a heteroaryl; and $R_7$ is H or a C1-C6 alkyl, wherein any 1-3 carbon atoms of the aryl and heteroaryl are linked to a substituent that is the same or different and is independently selected from H, F, Cl, Br, I, nitro, a C1-C6 alkyl and C1-C6 alkoxy.

In still another aspect, there is provided an agonist of cystic fibrosis conductance transmembrane regulator (CFTR), including the indolizino[3,2-c]quinoline derivative represented by Chemical Formula 1 or pharmaceutically acceptable salt thereof as an active ingredient.

In still another aspect, there is provided a pharmaceutical composition for preventing or treating diseases caused by degradation of activity of cystic fibrosis conductance transmembrane regulator, including the indolizino[3,2-c]quinoline derivative represented by Chemical Formula 1 or pharmaceutically acceptable salt thereof as an active ingredient.

In yet another aspect, there is provided a pharmaceutical composition for stimulating stem cell proliferation, including the indolizino[3,2-c]quinoline derivative represented by Chemical Formula 1 or pharmaceutically acceptable salt thereof as an active ingredient.

The present disclosure provides an indolizino[3,2-c]quinoline derivative having a novel structure and a method for preparing the same. The indolizino[3,2-c]quinoline derivative disclosed herein may function as an agonist of cystic fibrosis conductance transmembrane regulator and stimulates stem cell proliferation to function as an stem cell activator. Therefore, a pharmaceutical composition including the indolizino[3,2-c]quinoline derivative or a pharmaceutically acceptable salt thereof as an active ingredient may be useful for preventing or treating diseases caused by degradation of activity of cystic fibrosis conductance transmembrane regulator, such as cystic fibrosis, dry eye syndrome, constipation, hereditary hemochromatosis, coagulation-fibrin decomposition deficiency, myeloperoxidase deficiency, melanoma, chronic obstructive lung disease, Sjogren's syndrome, polycystic kidney disease, amyotrophic lateral sclerosis, progressive supranuclear palsy, Pick's disease, Alzheimer's disease, Parkinson's disease, Huntington's disease, myotonic dystrophy, spongiform encephalopathy, Fabry disease and Straussler-Scheinker disease.

DETAILED DESCRIPTION OF EMBODIMENTS

Figure 1:
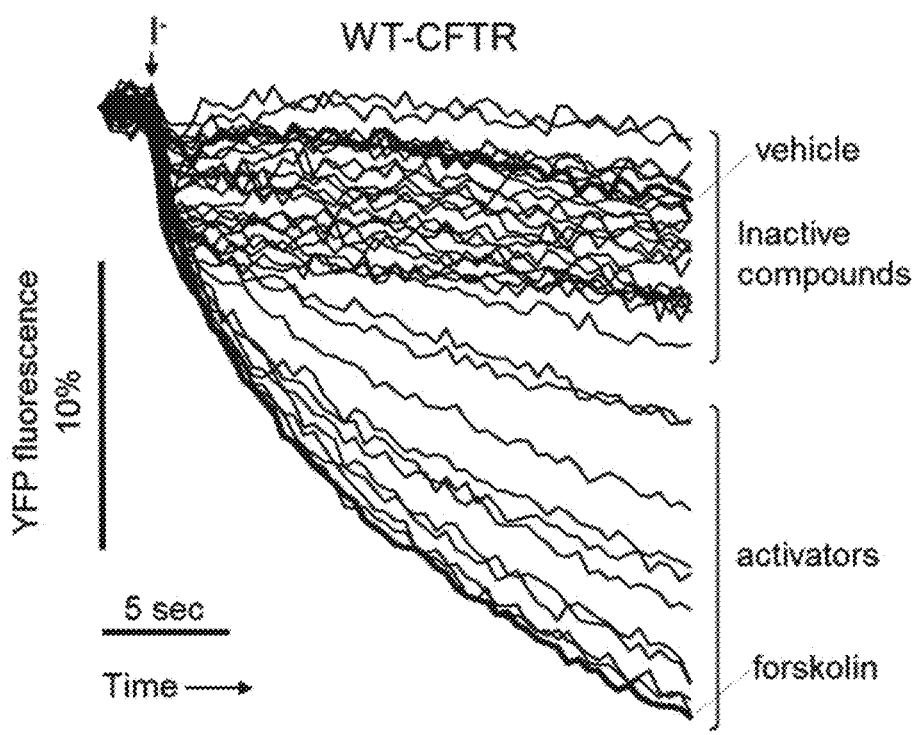
FIG. 1 is a graph illustrating the evaluation results of the chloride ion channel activity of cystic fibrosis conductance transmembrane regulator (CFTR), when using the compound according to an embodiment of the present disclosure.

The advantages, features and aspects of the present disclosure will become apparent from the following description of the embodiments.

In one aspect, there is provided an indolizino[3,2-c]quinoline derivative represented by the following Chemical Formula 1 or pharmaceutically acceptable salt thereof:

[Chemical Formula 1]

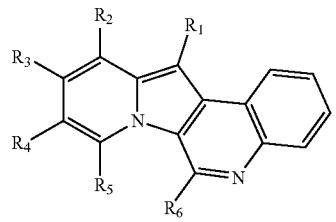

In Chemical Formula 1, $R_1$, $R_2$, $R_3$, $R_4$ and $R_5$ are the same or different, and each independently represents H, F, Cl, Br, I, a C1-C6 alkyl, C1-C6 alkoxy, $COOR_7$, aryl and a heteroaryl;

$R_6$ is selected from a C1-C6 alkyl, aryl and a heteroaryl; and $R_7$ is H or a C1-C6 alkyl, wherein any 1-3 carbon atoms of the aryl and heteroaryl are linked to a substituent that is the same or different and is independently selected from H, F, Cl, Br, I, nitro, a C1-C6 alkyl and C1-C6 alkoxy.

As used herein, aryl may be selected from phenyl, naphthyl, anthryl and biaryl, and heteroaryl may be selected from pyridyl, pyrimidyl, thiophenyl, pyrollyl and furanyl.

In addition, C1-C6 alkyl may be a linear or branched alkyl and particularly selected from the group consisting of methyl, ethyl, n-propyl, isopropyl, n-butyl, isobutyl, tert-butyl, n-propyl, isopropyl, n-hexyl and isohexyl.

As used herein, C1-C6 alkoxy may be selected from the group consisting of methoxy, ethoxy, propoxy, butoxy and pentoxy.

According to the present disclosure, the pharmaceutically acceptable salt is not particularly limited as long as it is used generally in the art, and particular examples thereof may include salts formed by using a nontoxic inorganic acid, such as hydrochloric acid, hydrobromic acid, sulfonic acid, amidosulfonic acid, phosphoric acid and nitric acid, and salts formed by using a nontoxic organic acid, such as acetic acid, propionic acid, succinic acid, glycolic acid, stearic acid, lactic acid, tartaric acid, citric acid, paratoluenesulfonic acid and methanesulfonic acid.

According to the present disclosure, the compound represented by Chemical Formula 1 may be at least one compound selected from the group consisting of the following Chemical Formula 6 through Chemical Formula 49, but is not limited thereto.

[Chemical Formula 6]

[Chemical Formula 7]

[Chemical Formula 8]

[Chemical Formula 9]

[Chemical Formula 10]

[Chemical Formula 11]

[Chemical Formula 12]

[Chemical Formula 13]

[Chemical Formula 14]

[Chemical Formula 15]

[Chemical Formula 16]
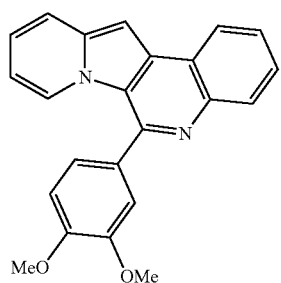
[Chemical Formula 17]
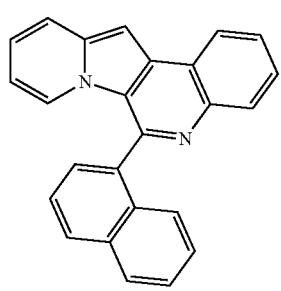
[Chemical Formula 18]
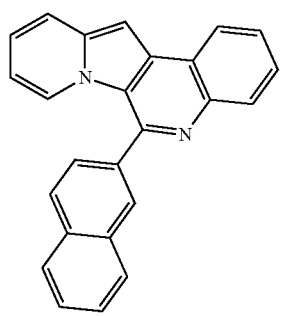
[Chemical Formula 19]
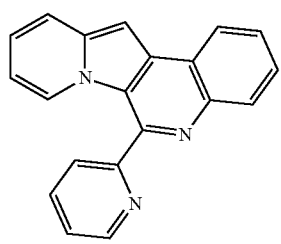
[Chemical Formula 20]
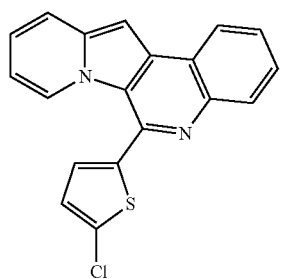
[Chemical Formula 21]
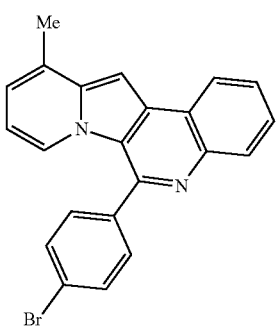
[Chemical Formula 22]
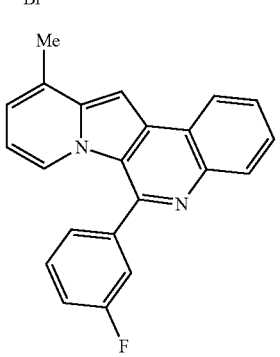
[Chemical Formula 23]
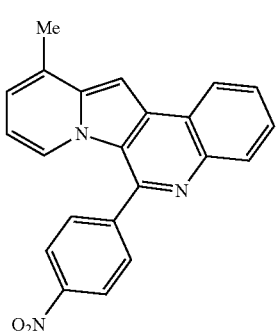
[Chemical Formula 24]
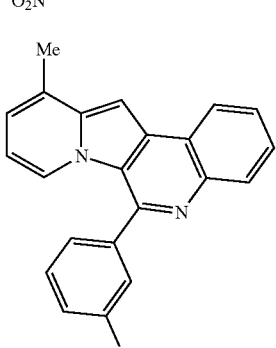
[Chemical Formula 25]
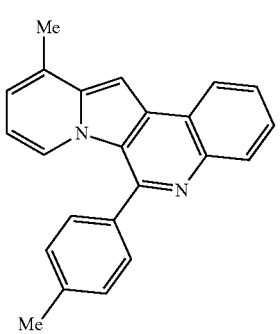

[Chemical Formula 26]
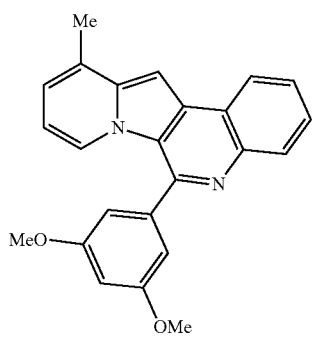
[Chemical Formula 27]
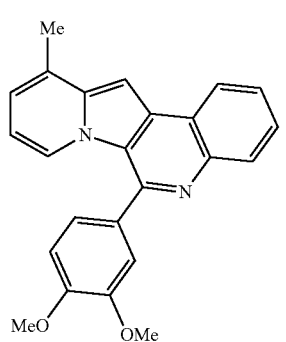
[Chemical Formula 28]
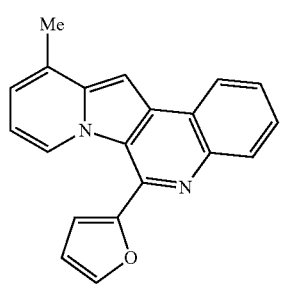
[Chemical Formula 29]
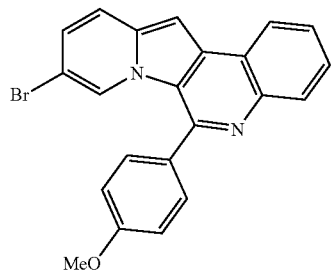
[Chemical Formula 30]
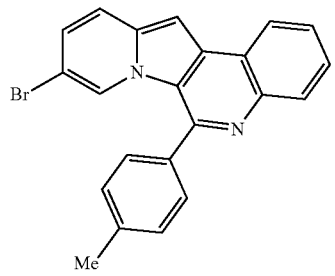
[Chemical Formula 31]
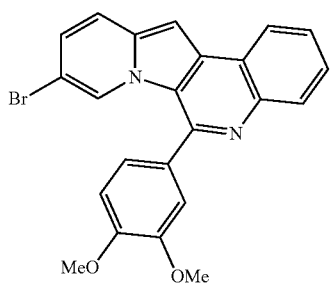
[Chemical Formula 32]
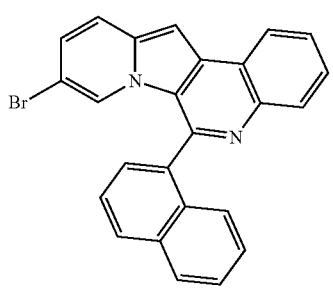
[Chemical Formula 33]
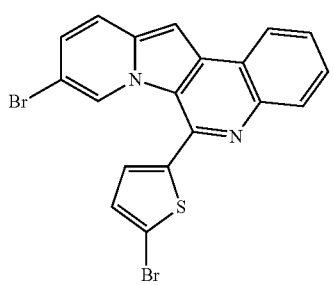
[Chemical Formula 34]
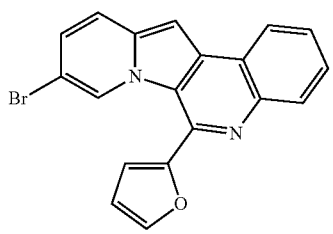
[Chemical Formula 35]
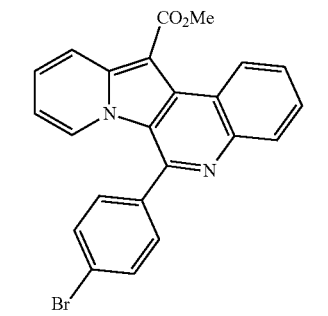

[Chemical Formula 36]
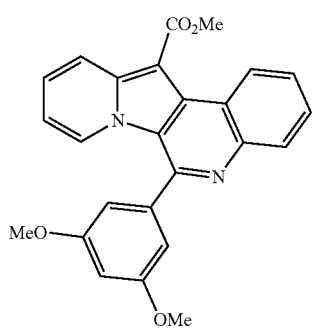
[Chemical Formula 37]
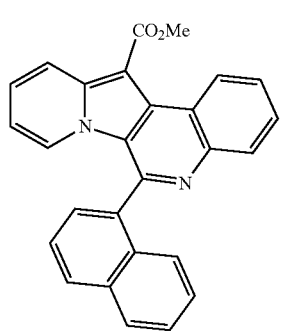
[Chemical Formula 38]
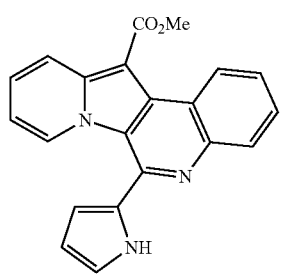
[Chemical Formula 39]
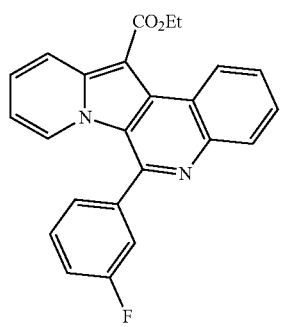
[Chemical Formula 40]
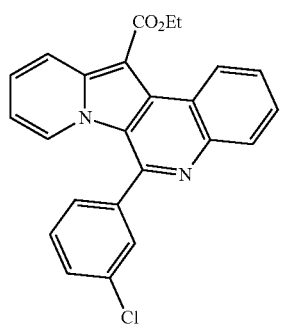
[Chemical Formula 41]
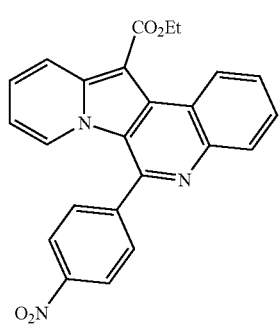
[Chemical Formula 42]
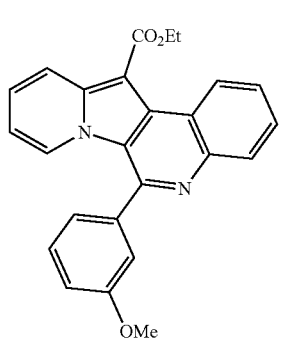
[Chemical Formula 43]
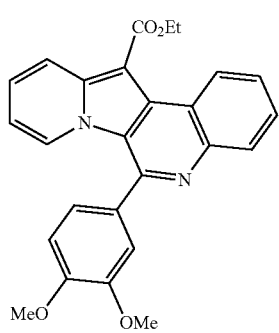
[Chemical Formula 44]
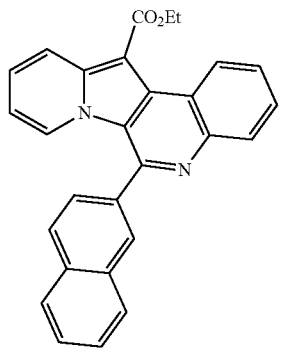
[Chemical Formula 45]
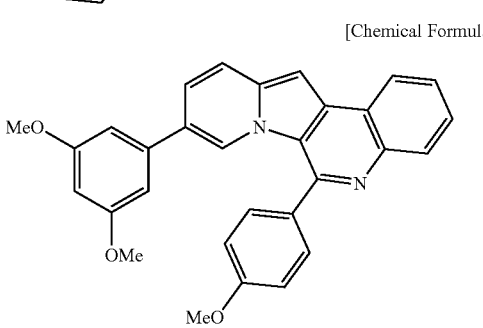

-continued

[Chemical Formula 46]

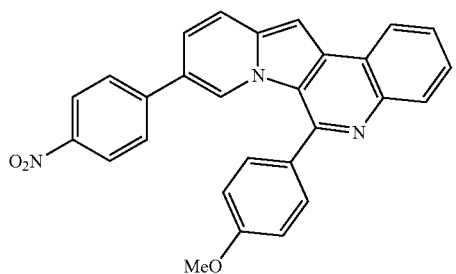

[Chemical Formula 47]

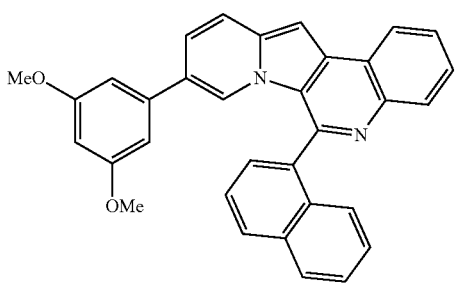

[Chemical Formula 48]

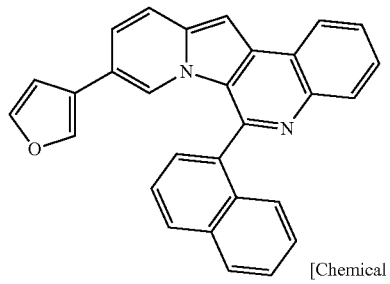

[Chemical Formula 49]

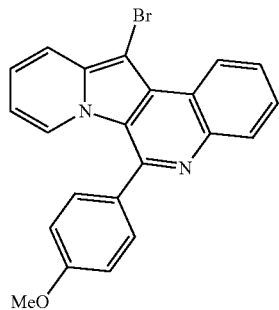

In another aspect, there is provided a method for preparing an indolizino[3,2-c]quinoline derivative represented by the following Chemical Formula 1 by reacting a compound represented by the following Chemical Formula 2 with an aldehyde in the presence of a catalyst:

[Chemical Formula 1]

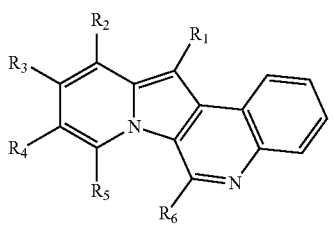

[Chemical Formula 2]

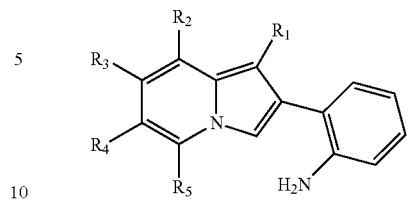

In Chemical Formula 1 or Chemical Formula 2, $R_1$, $R_2$, $R_3$, $R_4$, $R_5$ and $R_6$ are the same as defined above.

According to the present disclosure, the catalyst may be any one selected from $FeCl_3$, $AlCl_3$, $BiCl_3$, $InCl_3$, PTSA (p-toluenesulfonic acid) and PPTS (pyridinium p-toluenesulfonic acid). Particularly, the catalyst may be $FeCl_3$, since it generates no side product and allows production of the compound represented by Chemical Formula 1 with high yield.

According to the present disclosure, the side product that may be generated during the production of the compound represented by Chemical Formula 1 may be a compound represented by the following Chemical Formula 50:

[Chemical Formula 50]

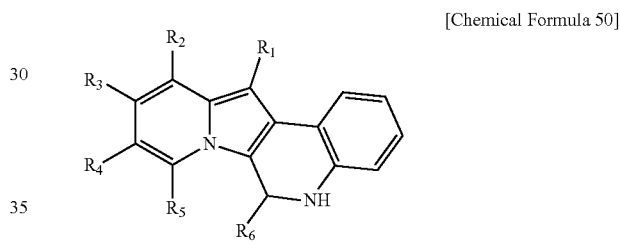

In addition, the catalyst may be used in an amount of 0.1-0.3 equivalents. When the catalyst is used in an amount less than 0.1 equivalents, such a small amount of catalyst cannot provide good reactivity. When the catalyst is used in an amount larger than 0.3 equivalents, reactivity decreases undesirably.

Meanwhile, the reaction may be carried out in a solvent selected from the group consisting of methylene chloride, N,N-dimethylformamide and tetrahydrofuran at 20-80° C. Particularly, the reaction may be carried out in dichloromethane as a solvent at 40-80° C. to improve the yield of reaction.

According to an embodiment, the aldehyde may be selected from C1-C6 alkyl aldehyde, aryl aldehyde and heteroaryl aldehyde, but is not limited thereto.

Particular examples of such aldehydes may include, but is not limited to: 4-bromobenzaldehyde, 4-fluorobenzaldehyde, 3-fluorobenzaldehyde, 4-chlorobenzaldehyde, 3-chlorobenzaldehyde, 4-nitrobenzaldehyde, benzaldehyde, 4-methoxybenzaldehyde, 3-methoxybenzaldehyde, 4-methylbenzaldehyde, 3,5-dimethoxybenzaldehyde, 3,4-dimethoxybenzaldehyde, 1-naphthylaldehyde, 2-naphthylaldehyde, picoline aldehyde, 5-bromothiophene-2-carbaldehyde, 5-chlorothiophene-2-carbaldehyde, furan-2-cabaldehyde and 1H-pyrrole-2-carbaldehyde.

Meanwhile, the compound represented by the above Chemical Formula 2 may be obtained by reducing a compound represented by the following Chemical Formula 3:

[Chemical Formula 3]

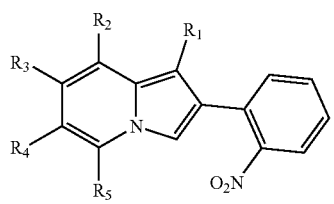

According to the present disclosure, the reduction may be carried out in at least one solvent selected from the group consisting of acetonitrile, water, C1-C4 alcohol, tetrahydrofuran and acetone at room temperature. Preferably, the reduction may be carried out in a mixed solvent of acetonitrile with water. More preferably, the reduction may be carried out in a solvent containing acetonitrile and water at a ratio of 7:3-3:7 in view of a high reaction rate and high yield.

In addition, any conventional reducing agent may be used for the reduction. Preferably, the reducing agent may be sodium hydrosulfite ($Na_2S_2O_4$). Use of sodium hydrosulfite is preferred in view of high reactivity without side reaction and high reaction yield.

Further, a base may be further added during the reduction. The base used for the reduction may be any one selected from KOAc and $K_2CO_3$. Particularly, use of $K_2CO_3$ as a base is preferred because it causes little side reaction and can provide a target compound with high yield.

Meanwhile, the compound represented by the above Chemical Formula 3 may be obtained by reacting a compound represented by the following Chemical Formula 4 with a compound represented by the following Chemical Formula 5:

[Chemical Formula 4]

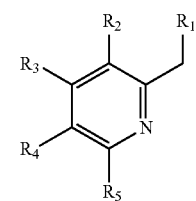

[Chemical Formula 5]

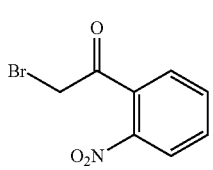

According to the present disclosure, the reaction may be carried out in at least one solvent selected from the group consisting of acetone, C1-C4 lower alcohol, tetrahydrofuran, dichloromethane and N,N-dimethylformamide at 60-120° C. Particularly, the reaction may be carried out in acetone as a solvent at 70-110° C. to obtain high yield without side reaction.

According to an embodiment, a base may be further added during the reaction. The reaction may be carried out by adding such a base together with a compound represented by Chemical Formula 4 and a compound represented by Chemical Formula 5. In a variant, a compound represented by Chemical Formula 4 is allowed to react with a compound represented by Chemical Formula 5 to form a reaction intermediate, and then a base may be added thereto.

When a base is added together during the reaction, the base may be $NaHCO_3$.

In addition, when a reaction intermediate is formed before a base is added, the base may be any one selected from triethylamine, 3,5-dimethylpyridine, 2,4-dimethylpyridine, N,N-dimethylaminopyridine, pyridine and hexamethylphosphoric triamide. Preferably, the base may be triethylamine and acetonitrile may be used as a reaction solvent to obtain high yield without side reaction.

According to an embodiment, when $R_1$ is H, it is preferred that the reaction is carried out by reacting a compound represented by Chemical Formula 4 with a compound represented by Chemical Formula 5 to form a reaction intermediate, and then adding a base thereto. Herein, the reaction intermediate may be a compound represented by the following Chemical Formula 51:

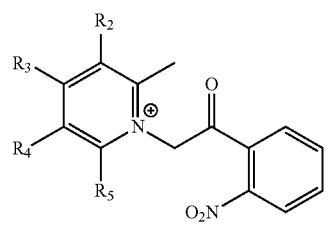

The above-described process is depicted by the following Reaction Scheme 1:

[Reaction Scheme 1]

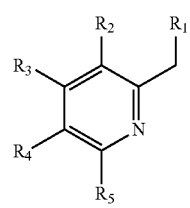 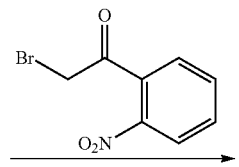 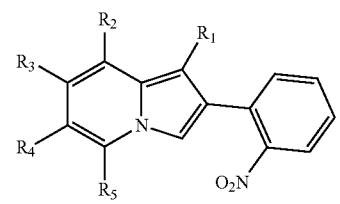

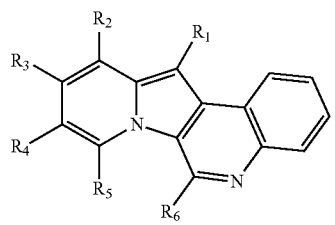 ← 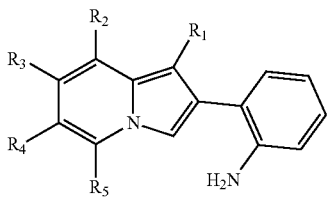

Meanwhile, in Chemical Formula 1, $R_1$ may be selected from H, F, Cl, Br, I, C1-C6 alkyl, C1-C6 alkoxy, COOR$_7$, aryl and heteroaryl. When $R_1$ is H, N-bromosuccinimide may be added in the presence of an organic solvent to carry out bromination, and substitution with another substituent may be carried out to introduce a functional group to the compound.

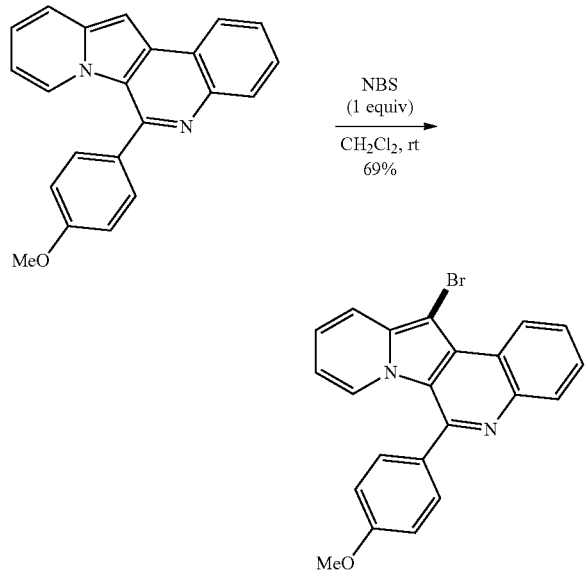

In addition, in Chemical Formula 1, $R_4$ may be selected from H, F, Cl, Br, I, C1-C6 alkyl, C1-C6 alkoxy, COOR7, aryl and heteroaryl. When $R_4$ is Br, the compound may be reacted with an aryl borate compound in the presence of a palladium catalyst and base to carry out arylation of $R_4$.

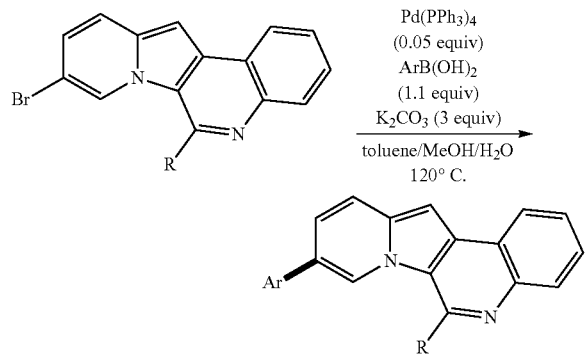

In still another aspect, there is provided an agonist of cystic fibrosis conductance transmembrane regulator (CFTR), including an indolizino[3,2-c]quinoline derivative represented by the above Chemical Formula 1 or a pharmaceutically acceptable salt thereof.

The indoliziono[3,2-c]quinoline derivative represented by Chemical Formula 1 or a pharmaceutically acceptable salt thereof can activate cystic fibrosis conductance transmembrane regulator. Therefore, the indoliziono[3,2-c]quinoline derivative represented by Chemical Formula 1 or a pharmaceutically acceptable salt thereof may function effectively in preventing or treating diseases caused by degradation of activity of cystic fibrosis conductance transmembrane regulator.

The diseases caused by degradation of activity of cystic fibrosis conductance transmembrane regulator may be at least one selected from cystic fibrosis, dry eye syndrome, constipation, hereditary hemochromatosis, coagulation-fibrin decomposition deficiency, myeloperoxidase deficiency, melanoma, chronic obstructive lung disease, Sjogren's syndrome, polycystic kidney disease, amyotrophic lateral sclerosis, progressive supranuclear palsy, Pick's disease, Alzheimer's disease, Parkinson's disease, Huntington's disease, myotonic dystrophy, spongiform encephalopathy, Fabry disease and Straussler-Scheinker disease.

The indoliziono[3,2-c]quinoline derivative represented by Chemical Formula 1 or a pharmaceutically acceptable salt thereof can stimulate proliferation and migration ability of stem cells. Therefore, the indoliziono[3,2-c]quinoline derivative represented by Chemical Formula 1 or a pharmaceutically acceptable salt thereof may function as a stem cell activator.

According to an embodiment, the stem cell may be any one of adipose-derived stem cells, neural stem cells, mesenchymal stem cells and adult stem cells.

According to an embodiment, the indoliziono[3,2-c] quinoline derivative or a pharmaceutically acceptable salt thereof may be mixed with a currently used carrier, adjuvant or diluent and formulated by a conventional formulation method to provide formulations suitable for oral administration or parenteral administration.

Particular examples of the carrier, adjuvant or diluent may include lactose, dextrose, sucrose, sorbitol, mannitol, xylitol, erythritol, maltitol, starch, alginate, gelatin, calcium phosphate, calcium silicate, cellulose, methyl cellulose, amorphous cellulose, polyvinyl pyrrolidone, water, methylhydroxybenzoate, propylhydroxybenzoate, talc, magnesium stearate and mineral oil.

In addition, such formulation may be carried out by further incorporating a currently used filler, bulking agent, binder, wetting agent, disintegrating agent, surfactant, or the like. A lubricant, such as magnesium stearate or talc, may be further incorporated.

In the case of oral administration, formulations, such as tablets, capsules, solutions, syrup or suspension, may be used. In the case of parenteral administration, formulations, such as intraperitoneal, subcutaneous, intramuscular or transdermal injection formulations, may be used.

According to an embodiment, the daily effective dose of the indolizino[3,2-c]quinoline derivative represented by Chemical Formula 1 or a pharmaceutically acceptable salt thereof may be 0.01-1000 mg/day based on adults. However, the administration dose may be varied depending on the age, body weight or sex of a patient, administration type, physical condition and severity of disease, and may be administered once to several times per day at a predetermined time interval depending on the judgement of a physician or pharmacist.

In still another aspect, there is provided a pharmaceutical composition including the target compound according to the present disclosure.

In still another aspect, there is provided use of the target compound for preparing a medicine for treating diseases caused by degradation of activity of cystic fibrosis conductance transmembrane regulator.

In still another aspect, there is provided a method for treating or preventing diseases caused by degradation of activity of cystic fibrosis conductance transmembrane regulator, the method including administering the target compound or pharmaceutical composition containing the same to a mammal.

In still another aspect, there is provided use of the target compound for preparing a medicine effective for stimulating proliferation of stem cells.

In still another aspect, there is provided a method effective for stimulating proliferation of stem cells, the method including administering the target compound or pharmaceutical composition containing the same to a mammal.

Hereinafter, the present disclosure will be explained in detail with reference preferred embodiments. However, the following examples are for illustrative purposes only and not intended to limit the scope of this disclosure.

EXAMPLES

Unless otherwise defined, all reagents are commercially available, purchased from commercial sources and used as they are without additional purification. 'Concentration' means removing a solvent through distillation by using a rotary evaporator. 'Drying' means adding a drying agent, such as anhydrous magnesium sulfate, or passing a subject through a space having a drying agent to remove moisture, followed by filtering. Flash chromatography is carried out by using silica gel with 230-400 mesh and a solvent, such as hexane, ethyl acetate or dichloromethane. All reactions are checked in terms of degree of reaction progress by using thin film chromatography. The compounds obtained from the inventive examples are determined by using 400 MHz nuclear magnetic resonance spectrometry and are expressed by chemical shift, multiplicity, coupling constant in a unit of Hz, and the number of hydrogen atoms. Molecular weights are measured by using Electrospray Ionization (ESI) and Quadrapole Time-of-Flight (Q-TOF) mass spectrometry.

Preparation Examples

Preparation Example 1.1

Preparation of 2-(2-Nitrophenyl)indolizine

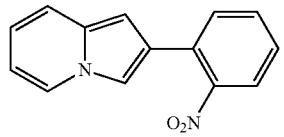

First, 4.1 mmol of 2-bromo-2'-nitroacetophenone and 5.33 mmol (1.3 eq.) of picoline are dissolved into 12 ml of acetone and the reaction mixture is allowed to react at 90° C. for 3 hours. After the completion of the reaction, the reaction mixture is cooled at room temperature and filtered, and then the filtered solid is washed with 5 ml of dichloromethane. To 20 ml of acetonitrile, 4.1 mmol of the obtained solid and 20.5 mmol (5 eq.) of triethylamine are added. Then, the reaction mixture is allowed to react at 60° C. for 16 hours. After the completion of the reaction, the reaction mixture is concentrated under reduced pressure, and then the concentrated reaction mixture is purified by silica gel column chromatography using hexane:ethyl acetate:dichloromethane=30:1:2 as a solvent to obtain the target compound.

Orange solid, mp 104.6-105.3° C. (891.0 mg, 85%); IR (ATR) v=3065, 2922, 1604, 1517, 1454, 1357 cm$^{-1}$; $^1$H NMR (400 MHz, CDCl$_3$) δ 7.86 (d, J=6.8 Hz, 1H), 7.66 (d, J=8.0 Hz, 1H), 7.61-7.49 (m, 2H), 7.43-7.35 (m, 2H), 7.33 (d, J=8.8 Hz, 1H), 6.67 (t, J=6.8 Hz, 1H), 6.53-6.41 (m, 2H); $^{13}$C NMR (100 MHz, CDCl$_3$) δ 133.3, 131.9, 131.7, 129.7, 127.4, 125.2, 123.8, 123.5, 119.4, 117.9, 111.2, 110.9, 98.7; HRMS (ESI) calcd for C$_{14}$H$_{11}$N$_2$O$_2$ 239.0815 ([M+H]$^+$). found 239.0813.

Preparation Example 1.2

Preparation of 8-Methyl-2-(2-nitrophenyl)indolizine

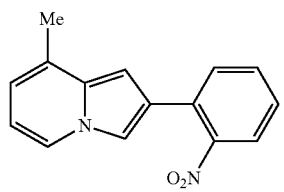

The target compound is obtained in the same manner as Preparation Example 1.1.

Orange solid, mp 104.6-105.3° C. (1010.1 mg, 91%); IR (ATR) v=3069, 2970, 1606, 1521, 1431, 1353 cm$^{-1}$; $^1$H NMR (400 MHz, CDCl$_3$) δ 7.77 (d, J=6.4 Hz, 1H), 7.67 (d, J=8.0 Hz, 1H), 7.61 (d, J=7.6 Hz, 1H), 7.55 (t, J=8.0 Hz, 1H), 7.40 (s, 1H), 7.38 (t, J=8.0 Hz, 1H), 6.49 (d, J=6.0 Hz, 1H), 6.45 (s, 1H), 6.44 (t, J=6.4 Hz, 1H), 2.39 (s, 3H); $^{13}$C NMR (100 MHz, CDCl$_3$) δ 134.4, 132.0, 131.7, 129.8, 128.5, 127.3, 123.5, 123.3, 123.2, 117.1, 111.4, 111.3, 97.36, 97.35, 18.2; HRMS (ESI) calcd for $C_{15}H_{13}N_2O_2$ 253.0972 ([M+H]$^+$). found 253.0969.

Preparation Example 1.3

Preparation of 6-Bromo-2-(2-nitrophenyl)indolizine

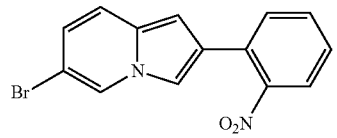

The target compound is obtained in the same manner as Preparation Example 1.1.

Orange gum (1367.5 mg, 98%); IR (ATR) ν=3094, 2922, 1607, 1517, 1426, 1324, 698 cm$^{-1}$; $^1$H NMR (400 MHz, CDCl$_3$) δ 8.02 (d, J=8.0 Hz, 1H), 7.69 (d, J=7.6 Hz, 1H), 7.59-7.51 (m, 2H), 7.44-7.38 (m, 1H), 7.37 (s, 1H), 7.25-7.18 (m, 1H), 6.74 (d, J=9.2 Hz, 1H), 6.51 (s, 1H); $^{13}$C NMR (100 MHz, CDCl$_3$) δ 131.92, 131.88, 131.5, 129.2, 127.7, 125.0, 124.6, 123.6, 121.4, 120.0, 111.3, 106.2, 100.2; HRMS (ESI) calcd for $C_{14}H_{10}BrN_2O_2$ 316.9920 ([M+H]$^+$). found 316.9918.

Preparation Example 1.4

Preparation of Methyl-2-(2-nitrophenyl)indolizine-1-carboxylate

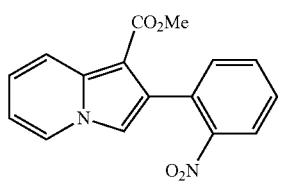

First, 2.2 mmol of 2-bromo-2'-nitroacetophenone, 3.3. mmol (1.5 eq.) of 2-pyridylacetate and 4.4 mmol (2 eq.) of NaHCO$_3$ are dissolved into 10 ml of acetone and the reaction mixture is allowed to react at 90° C. for 16 hours. After the completion of the reaction, the reaction mixture is concentrated under reduced pressure, dissolved into 10 ml of dichloromethane, and washed with 10 ml of water to remove impurities. Then, 10 ml of dichloromethane is added to the aqueous layer to carry out extraction once more. The resultant organic layer is dried over magnesium sulfate, concentrated under reduced pressure, and purified by silica gel column chromatography using hexane:ethyl acetate:dichloromethane=10:1:2 as a solvent to obtain the target compound.

Yellow solid, mp 147.2-148.2° C. (495.4 mg, 76%); IR (ATR) ν=3081, 2982, 1685, 1504, 1346, 1220 cm$^{-1}$; $^1$H NMR (400 MHz, CDCl$_3$) δ 8.19 (d, J=9.2 Hz, 1H), 8.05 (d, J=8.4 Hz, 1H), 7.98 (d, J=6.8 Hz, 1H), 7.59 (t, J=7.2 Hz, 1H), 7.49 (t, J=7.6 Hz, 1H), 7.41 (t, J=7.2 Hz, 1H), 7.07 (t, J=7.6 Hz, 1H), 6.72 (t, J=6.8 Hz, 1H), 3.67 (s, 3H); $^{13}$C NMR (100 MHz, CDCl$_3$) δ 164.9, 149.8, 136.6, 133.0, 132.3, 130.6, 128.4, 125.9, 124.2, 123.2, 120.5, 113.4, 113.0, 101.4, 50.8; HRMS (ESI) calcd for $C_{16}H_{13}N_2O_4$ 297.0870 ([M+H]$^+$). found 297.0872.

Preparation Example 1.5

Preparation of Ethyl-2-(2-nitrophenyl)indolizine-1-carboxylate

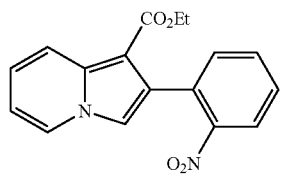

The target compound is obtained in the same manner as Preparation Example 1.4.

Orange solid, mp 117.3-117.8° C. (505.2 mg, 74%); IR (ATR) ν=3090, 2980, 1670, 1504, 1422, 1349, 1225 cm$^{-1}$; $^1$H NMR (400 MHz. CDCl$_3$) δ 8.22 (d, J=9.2 Hz, 1H), 8.06 (d, J=8.0 Hz, 1H), 8.00 (d, J=6.4 Hz, 1H), 7.60 (t, J=7.6 Hz, 1H), 7.50 (t, J=8.0 Hz, 1H), 7.42 (d, J=7.6 Hz, 1H), 7.27 (s, 1H), 7.09 (dd, J=7.2, 8.4 Hz, 1H), 6.75 (t, J=6.4 Hz, 1H), 4.13 (q, J=7.2 Hz, 2H), 1.12 (t, J=7.2 Hz, 3H); $^{13}$C NMR (100 MHz, CDCl$_3$) δ 164.5, 129.9, 136.5, 133.0, 132.3, 130.9, 128.3, 125.9, 124.1, 123.1, 120.5, 113.2, 113.0, 101.9, 59.6, 14.1; HRMS (ESI) calcd for $C_{17}H_{15}N_2O_4$ 311.1026 ([M+H]$^+$). found 311.1032.

Preparation Example 2.1

Preparation of 2-(Indolizin-2-yl)aniline

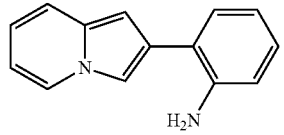 [SMILES: O=[N+]([O-])c1ccccc1-c1cc2ccccn2c1]

First, 1 mmol of the compound obtained from Preparation Example 1.1, mmol (5 eq.) of Na$_2$S$_2$O$_4$ and 5 mmol (5 eq.) of K$_2$CO$_3$ are dissolved into 10 ml of a mixed solvent containing acetonitrile/water (1:1) and agitated at room temperature for 2 hours. After the completion of the reaction, the reaction mixture is concentrated under reduced pressure. The concentrate is dissolved into 10 ml of dichloromethane and impurities are removed by using 10 ml of water. Then, 10 ml of dichloromethane is added to the aqueous layer to carry out extraction once more. The resultant organic layer is dried over magnesium sulfate and concentrated under reduced pressure to obtain the target compound.

Pale yellow solid, mp 141.8-142.6° C. (188.1 mg, 90%); IR (ATR) ν=3446, 3360, 3064, 2921, 1610, 1452, 1290 cm$^{-1}$; $^1$H NMR (400 MHz, CDCl$_3$) δ 7.91 (d, J=6.8 Hz, 1H), 7.47 (s, 1H), 7.36 (d, J=8.8 Hz, 1H), 7.31 (d, J=7.6 Hz, 1H), 7.12 (t, J=7.6 Hz, 1H), 6.82 (t, J=7.6 Hz, 1H), 6.78 (d, J=8.0 Hz, 1H), 6.68 (dd, J=6.8, 8.8 Hz, 1H), 6.60 (s, 1H), 6.47 (t, J=6.8 Hz, 1H), 4.04 (br s, 2H); $^{13}$C NMR (100 MHz. CDCl$_3$) δ 144.1, 133.2, 130.6, 128.0, 127.1, 125.1, 121.7, 119.0, 118.7, 117.5, 115.7, 111.1, 110.6, 99.0; HRMS (ESI) calcd for C$_{14}$H$_{13}$N$_2$ 209.1073 ([M+H]$^+$). found 209.1066.

Preparation Example 2.2

Preparation of 2-(8-Methylindolizin-2-yl)aniline

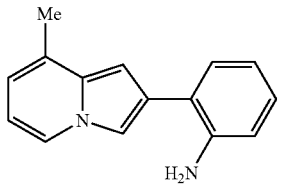

The target compound is obtained in the same manner as Preparation Example 2.1, except that the compound obtained from Preparation Example 1.2 is used instead of the compound obtained from Preparation Example 1.1.

Pale yellow solid, mp 113.8-114.6° C. (188.9 mg, 85%); IR (ATR) v=3439, 3350, 1610, 1477, 1452, 1369 cm$^{-1}$; $^1$H NMR (400 MHz, CDCl$_3$) δ 7.81 (d, J=6.8 Hz, 1H), 7.47 (s, 1H), 7.33 (d, J=7.2 Hz, 1H), 7.12 (t, J=7.6 Hz, 1H), 6.86-6.74 (m, 2H), 6.58 (s, 1H), 6.50 (d, J=6.4 Hz, 1H), 6.43 (t, J=6.4 Hz, 1H), 4.06 (br s, 2H), 2.41 (s, 3H); $^{13}$C NMR (100 MHz, CDCl$_3$) δ 144.1, 134.3, 130.6, 128.1, 128.0, 126.6, 123.1, 121.9, 118.8, 116.7, 115.8, 111.6, 110.7, 97.6, 18.3; HRMS (ESI) calcd for C$_{15}$H$_{15}$N$_2$ 223.1230 ([M+H]$^+$). found 223.1230.

Preparation Example 2.3

Preparation of 2-(6-Bromoindolizin-2-yl)aniline

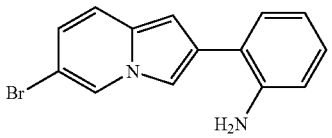

The target compound is obtained in the same manner as Preparation Example 2.1, except that the compound obtained from Preparation Example 1.3 is used instead of the compound obtained from Preparation Example 1.1.

Pale yellow solid, mp 130.8-131.2° C. (220.8 mg, 77%); IR (ATR) v=3407, 3331, 3018, 2922, 1607, 1476, 1450, 1354 cm$^{-1}$; $^1$H NMR (400 MHz, CDCl$_3$) δ 8.07 (s, 1H), 7.45 (s, 1H), 7.30-7.25 (m, 2H), 7.13 (t, J=7.6 Hz, 1H), 6.82 (t, J=7.6 Hz, 1H), 6.78 (d, J=8.0 Hz, 1H), 6.74 (d, J=9.2 Hz, 1H), 6.64 (s, 1H), 4.00 (br s, 2H); $^{13}$C NMR (100 MHz, CDCl$_3$) δ 144.1, 131.6, 130.6, 128.3, 127.8, 124.9, 121.1, 120.9, 119.6, 118.8, 115.9, 111.6, 105.5, 100.4; HRMS (ESI) calcd for C$_{14}$H$_{12}$BrN$_2$ 287.0178 ([M+H]$^+$). found 287.0177.

Preparation Example 2.4

Preparation of Methyl 2-(2-aminophenyl)indolizine-1-carboxylate

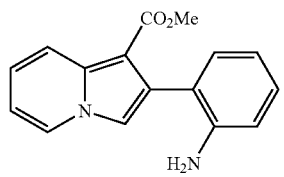

The target compound is obtained in the same manner as Preparation Example 2.1, except that the compound obtained from Preparation Example 1.4 is used instead of the compound obtained from Preparation Example 1.1.

Pale yellow solid, mp 278.3-279.3° C. (263.6 mg, 99%); IR (ATR) v=3477, 3384, 1679, 1613, 1477, 1435, 1367 cm$^{-1}$; $^1$H NMR (400 MHz, CDCl$_3$) δ 8.21 (d, J=9.2 Hz, 1H), 8.01 (d, J=6.8 Hz, 1H), 7.23 (s, 1H), 7.18 (t, J=7.6 Hz, 1H), 7.12 (d, J=7.6 Hz, 1H), 7.11-7.05 (m, 1H), 6.81 (d, J=7.6 Hz, 1H), 6.77 (d, J=8.4 Hz, 1H), 6.74 (d, J=6.8 Hz, 1H), 3.75 (s, 3H), 3.75 (br s, 2H); $^{13}$C NMR (100 MHz, CDCl$_3$) δ 165.3, 145.2, 131.0, 129.3, 128.8, 125.9, 122.8, 121.5, 120.3, 118.2, 115.4, 114.4, 112.9, 102.3, 50.9; HRMS (ESI) calcd for C$_{16}$H$_{15}$N$_2$O$_2$ 267.1128 ([M+H]$^+$). found 267.1130.

Preparation Example 2.5

Preparation of Ethyl-2-(2-aminophenyl)indolizine-1-carboxylate

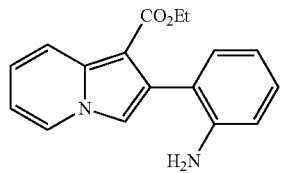 [SMILES: CCOC(=O)c1c(-c2ccccc2[N+](=O)[O-])cn2ccccc12]

The target compound is obtained in the same manner as Preparation Example 2.1, except that the compound obtained from Preparation Example 1.5 is used instead of the compound obtained from Preparation Example 1.1.

Pale yellow solid, mp 289.7-299.6° C. (229.9 mg, 82%); IR (ATR) v=3483, 3389, 3023, 2981, 1695, 1609, 1505, 1417, 1300 cm$^{-1}$; $^1$H NMR (400 MHz, CDCl$_3$) δ 8.23 (d, J=9.2 Hz, 1H), 7.98 (d, J=6.8 Hz, 1H), 7.22 (s, 1H), 7.16 (t, J=7.6 Hz, 1H), 7.11 (d, J=7.6 Hz, 1H), 7.10-7.03 (m, 1H), 6.83-6.68 (m, 3H), 4.20 (q, J=6.8 Hz, 2H), 3.72 (br s, 2H), 1.16 (t, J=6.8 Hz, 3H); $^{13}$C NMR (100 MHz, CDCl$_3$) δ 164.9, 145.2, 136.6, 130.9, 129.1, 128.6, 125.8, 122.6, 121.7, 120.2, 118.0, 115.2, 114.1, 112.8, 102.5, 59.4, 14.2; HRMS (ESI) calcd for C$_{17}$H$_{17}$N$_2$O$_2$ 281.1285 ([M+H]$^+$). found 281.1280.

EXAMPLES

Example 1

6-(4-Bromophenyl)indolizino[3,2-c]quinoline

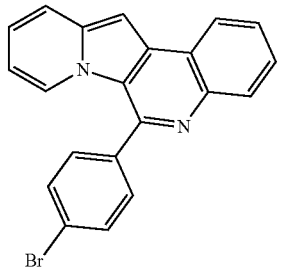 [SMILES: Brc1ccc(-c2nc3ccccc3c3cc4ccccn4c23)cc1]

First, 0.14 mmol of the compound according to Preparation Example 2.1, 0.17 mmol (1.2 eq.) of 4-bromobenzaldehyde and 0.028 mmol (0.2 eq.) of FeCl$_3$ are dissolved into 4 ml of dichloromethane and the reaction mixture is allowed to react at 60° C. for 16 hours. After the completion of the reaction, the reaction mixture is washed with 3 ml of water and the aqueous layer is extracted once more with 3 ml of dichloromethane. The organic layers are combined, dried over magnesium sulfate and concentrated under reduced pressure. The concentrated reaction mixture is purified by silica gel column chromatography using hexane:ethyl acetate:dichloromethane=30:1:2 as a solvent to obtain the target compound.

Yellow solid, mp 205.5-205.8° C. (43.4 mg, 83%); IR (ATR) ν=2921, 2852, 1630, 1480, 1354 cm$^{-1}$; $^1$H NMR (400 MHz, CDCl$_3$) δ 8.39 (d, J=7.6 Hz, 1H), 8.23 (d, J=8.0 Hz, 1H), 7.89 (d, J=6.8 Hz, 1H), 7.76 (d, J=8.0 Hz, 2H), 7.73-7.68 (m, 1H), 7.69-7.62 (m, 2H), 7.58 (d, J=8.0 Hz, 2H), 7.31 (s, 1H), 7.07 (t, J=7.6 Hz, 1H), 6.48 (d, J=6.8 Hz, 1H); $^{13}$C NMR (100 MHz. CDCl$_3$) δ 147.4, 143.1, 139.1, 138.9, 132.6, 131.9, 130.6, 129.7, 127.8, 126.8, 126.0, 123.7, 123.6, 122.5, 121.0, 119.5, 110.1, 92.4; HRMS (ESI) calcd for C$_{21}$H$_{14}$BrN$_2$ 373.0335 ([M+H]$^+$). found 373.0336.

Example 2

6-(4-Fluorophenyl)indolizino[3,2-c]quinoline

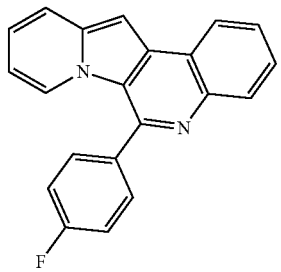 [SMILES: Fc1ccc(-c2nc3ccccc3c3cc4ccccn4c23)cc1]

The target compound is obtained in the same manner as Example 1, except that 4-fluorobenzaldehyde is used instead of 4-bromobenzaldehyde.

Yellow solid, mp 167.0-167.4° C. (24.5 mg, 56%); IR (ATR) ν=2920, 2850, 1601, 1489, 1355, 1225 cm$^{-1}$; $^1$H NMR (400 MHz, CDCl$_3$) δ 8.38 (d, J=8.0 Hz, 1H), 8.24 (d, J=8.0 Hz, 1H), 7.82 (d, J=7.2 Hz, 1H), 7.73-7.65 (m, 3H), 7.65-7.60 (m, 2H), 7.32 (d, J=8.8 Hz, 1H), 7.30 (d, J=9.2 Hz, 2H), 7.05 (dd, J=6.8, 8.8 Hz, 1H), 6.44 (t, J=6.8 Hz, 1H); $^{13}$C NMR (100 MHz, CDCl$_3$) δ 164.7, 162.2, 147.6, 143.1, 124.1, 139.0, 136.0, 131.8, 130.8 (d, J$_{C,F}$=8.0 Hz), 129.6, 126.8 (d, J$_{C,F}$=180.0 Hz), 126.7, 123.6 (d, J$_{C,F}$=9.0 Hz), 122.5, 121.2, 119.5, 116.5 (d, J$_{C,F}$=21.0 Hz), 110.0, 92.4; HRMS (ESI) calcd for C$_{21}$H$_{14}$FN$_2$ 313.1136 ([M+H]$^+$). found 313.1388.

Example 3

6-(4-Chlorophenyl)indolizino[3,2-c]quinoline

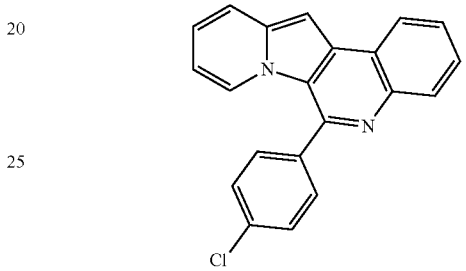

The target compound is obtained in the same manner as Example 1, except that 4-chlorobenzaldehyde is used instead of 4-bromobenzaldehyde.

Yellow solid, mp 190.5-191.0° C. (25.3 mg, 55%); IR (ATR) ν=3054, 2921, 2852, 1631, 1482, 1091, 728 cm$^{-1}$; $^1$H NMR (400 MHz, CDCl$_3$) δ 8.35 (d, J=8.0 Hz, 1H), 8.23 (d, J=8.0 Hz, 1H), 7.84 (d, J=7.2 Hz, 1H), 7.69 (t, J=7.2 Hz, 1H), 7.65-7.53 (m, 6H), 7.26 (s, 1H), 7.04 (t, J=6.8 Hz, 1H), 6.45 (t, J=6.8 Hz, 1H); $^{13}$C NMR (100 MHz, CDCl$_3$) δ 147.3, 143.0, 139.1, 138.4, 135.4, 131.8, 130.3, 129.61, 129.56, 127.7, 126.7, 126.0, 123.64, 123.61, 122.5, 121.0, 119.4, 110.1, 92.4; HRMS (ESI) calcd for C$_{21}$H$_{14}$ClN$_2$ 329.0840 ([M+H]$^+$). found 329.0839.

Example 4

6-(3-Chlorophenyl)indolizino[3,2-c]quinoline

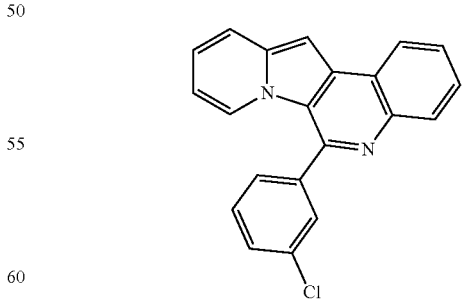

The target compound is obtained in the same manner as Example 1, except that 3-chlorobenzaldehyde is used instead of 4-bromobenzaldehyde.

Yellow solid, mp 124.3-125.3° C. (20.7 mg, 45%); IR (ATR) ν=3920, 2850, 1631, 1561, 1498, 1352, 721 cm$^{-1}$; $^1$H NMR (400 MHz, CDCl$_3$) δ 8.40 (d, J=8.0 Hz, 1H), 8.25 (d, J=8.0 Hz, 1H), 7.84 (d, J=7.2 Hz, 1H), 7.75 (m, 2H), 7.69-7.61 (m, 2H), 7.61-7.53 (m, 3H), 7.31 (s, 1H), 7.07 (dd, J=6.8, 8.8 Hz, 1H), 6.47 (t, J=7.2 Hz, 1H); $^{13}$C NMR (100 MHz, CDCl$_3$) δ 135.3, 131.7, 130.6, 130.5, 129.9, 129.5, 129.4, 129.3, 129.0, 128.0, 127.6, 126.9, 126.6, 126.2, 125.9, 123.5, 122.4, 119.3, 110.0, 92.3, 77.2; HRMS (ESI) calcd for C$_{21}$H$_{14}$ClN$_2$ 329.0840 ([M+H]$^+$). found 329.0834.

Example 5

6-(4-Nitrophenyl)indolizino[3,2-c]quinoline

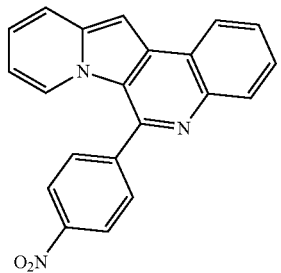 [SMILES: O=[N+]([O-])c1ccc(-c2nc3ccccc3c3cc4ccccn4c23)cc1]

The target compound is obtained in the same manner as Example 1, except that 4-nitrobenzaldehyde is used instead of 4-bromobenzaldehyde.

Orange solid, mp 246.3-246.5° C. (26.1 mg, 55%); IR (ATR) v=2921, 2850, 1632, 1596, 1505, 1434, 1343 cm$^{-1}$; $^1$H NMR (400 MHz, CDCl$_3$) δ 8.47 (d, J=8.5 Hz, 2H), 8.39 (d, J=7.6 Hz, 1H), 8.22 (d, J=8.0 Hz, 1H), 7.89 (d, J=8.5 Hz, 2H), 7.77 (d, J=6.8 Hz, 1H), 7.72 (t, J=7.6 Hz, 1H), 7.69-7.62 (m, 2H), 7.31 (s, 1H), 7.08 (dd, J=7.2, 8.4 Hz, 1H), 6.48 (t, J=6.8 Hz, 1H); $^{13}$C NMR (100 MHz, CDCl$_3$) δ 148.4, 146.4, 145.9, 143.0, 139.2, 132.0, 130.2, 129.7, 128.0, 126.5, 126.4, 124.6, 123.8, 123.7, 122.6, 120.6, 119.7, 110.4, 92.7; HRMS (ESI) calcd for C$_{21}$H$_{14}$N$_3$O$_2$ 340.1081 ([M+H]$^+$). found 340.1080.

Example 6

6-Phenylindolizino[3,2-c]quinoline

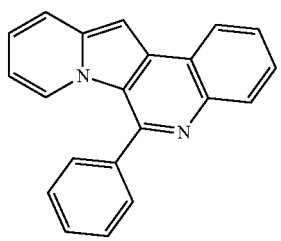 [SMILES: c1ccc(-c2nc3ccccc3c3cc4ccccn4c23)cc1]

The target compound is obtained in the same manner as Example 1, except that benzaldehyde is used instead of 4-bromobenzaldehyde.

Yellow solid, mp 141.9-142.8° C. (25.5 mg, 62%); IR (ATR) v=3046, 2941, 1631, 1487, 1353 cm$^{-1}$; $^1$H NMR (400 MHz, CDCl$_3$) δ 8.36 (d, J=8.0 Hz, 1H), 8.26 (d, J=8.4 Hz, 1H), 7.78 (d, J=7.2 Hz, 1H), 7.70 (d, J=6.8 Hz, 1H), 7.66 (dd, J=1.2, 8.0 Hz, 2H), 7.45-7.53 (m, 5H), 7.26 (s, 1H), 7.01 (dd, J=7.2, 8.8 Hz, 1H), 6.38 (t, J=6.4 Hz, 1H); $^{13}$C NMR (100 MHz, CDCl$_3$) δ 148.8, 143.2, 140.0, 139.0, 131.7, 129.7, 129.4, 129.3, 128.8, 127.6, 126.9, 125.8, 123.6, 123.5, 122.5, 121.2, 119.3, 109.8, 92.2; HRMS (ESI) calcd for C$_{21}$H$_{15}$N$_2$ 295.1230 ([M+H]$^+$). found 295.1225.

Example 7

6-(4-Methoxyphenyl)indolizino[3,2-c]quinoline

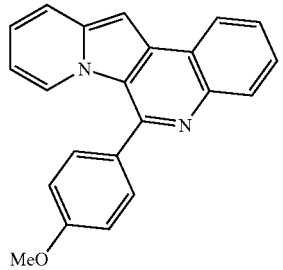 [SMILES: COc1ccc(-c2nc3ccccc3c3cc4ccccn4c23)cc1]

The target compound is obtained in the same manner as Example 1, except that 4-methoxybenzaldehyde is used instead of 4-bromobenzaldehyde.

Yellow solid, mp 164.3-164.7° C. (29.5 mg, 65%); IR (ATR) v=3055, 2998, 1606, 1494, 1440, 1374, 1355, 1024 cm$^{-1}$; $^1$H NMR (400 MHz, CDCl$_3$) δ 8.38 (d, J=7.6 Hz, 1H), 8.24 (d, J=8.0 Hz, 1H), 7.94 (d, J=7.2 Hz, 1H), 7.69 (t, J=7.2 Hz, 1H), 7.66-7.56 (m, 4H), 7.28 (s, 1H), 7.14 (d, J=8.4 Hz, 2H), 7.04 (t, J=7.2 Hz, 1H), 6.43 (t, J=6.4 Hz, 1H), 3.94 (s, 3H): $^{13}$C NMR (100 MHz, CDCl$_3$) δ 160.4, 148.5, 143.2, 138.9, 132.3, 131.6, 130.1, 129.6, 127.5, 126.9, 125.6, 123.6, 123.4, 122.4, 121.4, 119.3, 114.8, 109.7, 92.1, 55.6; HRMS (ESI) calcd for C$_{22}$H$_{17}$N$_2$O 325.1335 ([M+H]$^+$). found 325.1338.

Example 8

6-(3-Methoxyphenyl)indolizino[3,2-c]quinoline

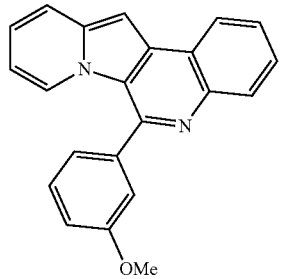 [SMILES: COc1cccc(-c2nc3ccccc3c3cc4ccccn4c23)c1]

The target compound is obtained in the same manner as Example 1, except that 3-methoxybenzaldehyde is used instead of 4-bromobenzaldehyde.

Yellow solid, mp 174.0-174.4° C. (23.6 mg, 52%); IR (ATR) v=3067, 2920, 1598, 1461, 1354, 1255 cm$^{-1}$; $^1$H NMR (400 MHz, CDCl$_3$) δ 8.39 (d, J=8.0 Hz, 1H), 8.26 (d, J=8.4 Hz, 1H), 7.83 (d, J=7.6 Hz, 1H), 7.70 (t, J=7.2 Hz, 1H), 7.64 (d, J=8.4 Hz, 2H), 7.52 (t, J=8.0 Hz, 1H), 7.30 (s, 1H), 7.25-7.18 (m, 2H), 7.13 (dd, J=1.6, 8.0 Hz, 1H), 7.05 (dd, J=6.8, 9.2 Hz, 1H), 6.43 (t, J=6.8 Hz, 1H), 3.88 (s, 3H); $^{13}$C NMR (100 MHz, CDCl$_3$) δ 160.5, 148.6, 143.1, 131.7, 131.5, 130.6, 129.71, 129.70, 127.7, 127.1, 125.8, 123.7, 123.6, 122.6, 121.1, 121.0, 119.3, 115.7, 113.6, 109.9, 92.2, 55.6; HRMS (ESI) calcd for C$_{22}$H$_{17}$N$_2$O 325.1335 ([M+H]$^+$). found 325.1328.

Example 9

6-(p-Tolyl)indolizino[3,2-c]quinoline

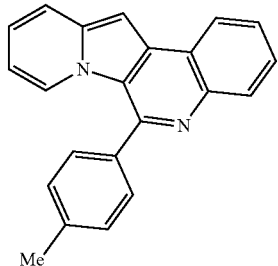 [SMILES: Cc1ccc(-c2nc3ccccc3c3cc4ccccn4c23)cc1]

The target compound is obtained in the same manner as Example 1, except that 4-methylbenzaldehyde is used instead of 4-bromobenzaldehyde.

Yellow solid, mp 85.3-86.0° C. (22.9 mg, 53%); IR (ATR) v=2980, 1631, 1492, 1435, 1372 cm$^{-1}$; $^1$H NMR (400 MHz, CDCl$_3$) δ 8.37 (d, J=8.4 Hz, 1H), 8.25 (d, J=8.4 Hz, 1H), 7.89 (d, J=7.2 Hz, 1H), 7.68 (t, J=7.6 Hz, 1H), 7.62 (d, J=8.4 Hz, 2H), 7.56 (d, J=7.2 Hz, 2H), 7.41 (d, J=7.6 Hz, 2H), 7.27 (s, 1H), 7.02 (t, J=8.8 Hz, 1H), 6.40 (t, J=6.8 Hz, 1H), 2.51 (s, 3H); $^{13}$C NMR (100 MHz, CDCl$_3$) δ 148.9, 143.2, 139.1, 138.9, 137.0, 131.6, 130.0, 129.7, 128.7, 127.5, 127.0, 125.7, 123.6, 123.4, 122.5, 121.3, 119.3, 109.7, 92.2, 21.7; HRMS (ESI) calcd for C$_{22}$H$_{17}$N$_2$ 309.1386 ([M+H]$^+$). found 309.1388.

Example 10

6-(3,5-Dimethoxyphenyl)indolizino[3,2-c]quinoline

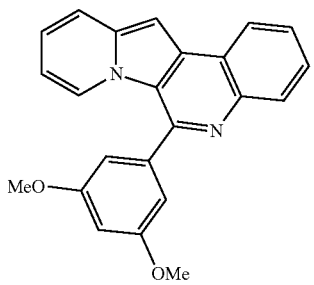 [SMILES: COc1cc(OC)cc(-c2nc3ccccc3c3cc4ccccn4c23)c1]

The target compound is obtained in the same manner as Example 1, except that 3,5-dimethoxybenzaldehyde is used instead of 4-bromobenzaldehyde.

Yellow solid, mp 139.7-140.4° C. (35.2 mg, 71%); IR (ATR) v=3062, 2838, 1592, 1452, 1353, 1149 cm$^{-1}$; $^1$H NMR (400 MHz, CDCl$_3$) δ 8.39 (d, J=7.6 Hz, 1H), 8.26 (d, J=8.4 Hz, 1H), 7.88 (d, J=7.2 Hz, 1H), 7.70 (t, J=7.2 Hz, 1H), 7.67-7.60 (m, 2H), 7.30 (s, 1H), 7.06 (dd, J=6.4, 8.8 Hz, 1H), 6.79 (d, J=2.0 Hz, 2H), 6.69-6.64 (m, 1H), 6.47 (t, J=6.8 Hz, 1H), 3.85 (s, 6H); $^{13}$C NMR (100 MHz, CDCl$_3$) δ 161.7, 148.5, 143.0, 141.7, 139.0, 131.6, 129.7, 127.6, 127.1, 125.8, 123.6, 123.6, 122.6, 120.9, 119.2, 110.0, 106.3, 101.9, 92.1, 55.7; HRMS (ESI) calcd for C$_{23}$H$_{19}$N$_2$O$_2$ 355.1441 ([M+H]$^+$). found 355.1431.

Example 11

6-(3,4-Dimethoxyphenyl)indolizino[3,2-c]quinoline

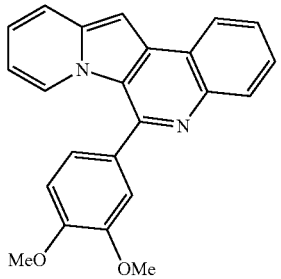 [SMILES: COc1ccc(-c2nc3ccccc3c3cc4ccccn4c23)cc1OC]

The target compound is obtained in the same manner as Example 1, except that 3,4-dimethoxybenzaldehyde is used instead of 4-bromobenzaldehyde.

Yellow solid, mp 91.3-92.0° C. (33.7 mg, 68%); IR (ATR) v=3053, 2933, 1602, 1493, 1450, 1352, 1135, 1022 cm$^{-1}$; $^1$H NMR (400 MHz, CDCl$_3$) δ 8.38 (d, J=8.0 Hz, 1H), 8.25 (d, J=8.4 Hz, 1H), 7.90 (d, J=7.2 Hz, 1H), 7.69 (t, J=7.6 Hz, 1H), 7.66-7.57 (m, 2H), 7.28 (s, 1H), 7.22 (dd, J=1.6, 8.4 Hz, 1H), 7.19 (s, 1H), 7.09 (d, J=8.4 Hz, 1H), 7.05 (t, J=6.8 Hz, 1H), 6.44 (t, J=6.8 Hz, 1H), 4.01 (s, 3H), 3.91 (s, 3H); $^{13}$C NMR (100 MHz, CDCl$_3$) δ 149.8, 149.7, 148.5, 143.1, 139.0, 132.4, 131.7, 129.6, 127.6, 127.1, 125.7, 123.6, 123.5, 122.5, 121.30, 121.23, 119.3, 111.9, 111.7, 109.8, 92.2, 56.24, 56.17; HRMS (ESI) calcd for C$_{23}$H$_{19}$N$_2$O$_2$ 355.1441 ([M+H]$^+$). found 355.1448.

Example 12

6-(Naphthalen-1-yl)indolizino[3,2-c]quinoline

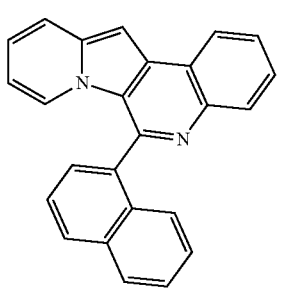 [SMILES: c1ccc2c(-c3nc4ccccc4c4cc5ccccn5c34)cccc2c1]

The target compound is obtained in the same manner as Example 1, except that 1-naphthaldehyde is used instead of 4-bromobenzaldehyde.

Yellow solid, mp 205.6-206.3° C. (40.0 mg, 83%); IR (ATR) v=3051, 2929, 1631, 1493, 760 cm$^{-1}$; $^1$H NMR (400 MHz, CDCl$_3$) δ 8.45 (d, J=7.6 Hz, 1H), 8.30 (d, J=8.0 Hz, 1H), 8.08 (d, J=7.2 Hz, 1H), 7.98 (d, J=8.4 Hz, 1H), 7.76-7.65 (m, 4H), 7.63 (d, J=9.0 Hz, 1H), 7.49 (t, J=7.6 Hz, 1H), 7.40 (d, J=8.4 Hz, 1H), 7.33 (s, 1H), 7.31-7.22 (m, 1H), 7.17 (d, J=7.2 Hz, 1H), 6.94 (t, J=7.6 Hz, 1H), 6.14 (t, J=6.8 Hz, 1H); $^{13}$C NMR (100 MHz, CDCl$_3$) δ 147.4, 143.4, 139.0, 137.0, 134.0, 131.6, 131.4, 129.8, 129.6, 128.6, 127.7, 127.3, 126.9, 126.6, 126.5, 126.1, 125.9, 125.3, 123.7, 123.5, 122.7, 122.3, 119.1, 110.0, 92.1; HRMS (ESI) calcd for $C_{25}H_{17}N_2$ 345.1386 ([M+H]$^+$). found 345.1383.

Example 13

6-(Naphthalen-2-yl)indolizino[3,2-c]quinoline

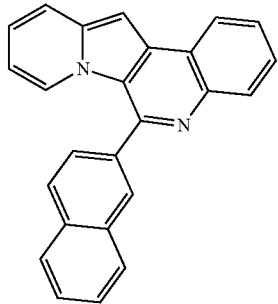 [SMILES: c1ccc2cc(-c3nc4ccccc4c4cc5ccccn5c34)ccc2c1]

The target compound is obtained in the same manner as Example 1, except that 2-naphthaldehyde is used instead of 4-bromobenzaldehyde.

Yellow solid, mp 205.6-206.2° C. (22.7 mg, 47%); IR (ATR) v=3047, 2920, 1632, 1496, 1352, 745 cm$^{-1}$; $^1$H NMR (400 MHz, CDCl$_3$) δ 8.41 (d, J=7.6 Hz, 1H), 8.28 (d, J=8.0 Hz, 1H), 8.21 (s, 1H), 8.08 (d, J=8.4 Hz, 1H), 7.99 (d, J=7.6 Hz, 1H), 7.95 (d, J=7.2 Hz, 1H), 7.84 (d, J=7.6 Hz, 1H), 7.75 (d, J=8.4 Hz, 1H), 7.71 (t, J=7.2 Hz, 1H), 7.67-7.59 (m, 3H), 7.59-7.54 (m, 1H), 7.31 (s, 1H), 7.01 (t, J=7.2 Hz, 1H), 6.32 (t, J=7.2 Hz, 1H); $^{13}$C NMR (100 MHz, CDCl$_3$) δ 143.3, 139.0, 137.4, 133.8, 133.6, 131.8, 129.7, 129.2, 128.7, 128.3, 128.1, 127.7, 127.0, 126.9, 126.8, 126.3, 125.9, 123.7, 123.5, 122.6, 121.4, 119.3, 109.9, 92.3; HRMS (ESI) calcd for $C_{25}H_{17}N_2$ 345.1386 ([M+H]$^+$). found 345.1387.

Example 14

6-(Pyridin-2-yl)indolizino[3,2-c]quinoline

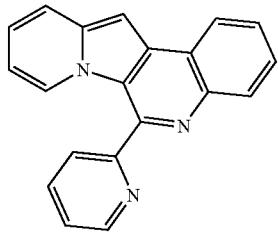 [SMILES: c1ccc(-c2nc3ccccc3c3cc4ccccn4c23)nc1]

The target compound is obtained in the same manner as Example 1, except that picoline aldehyde is used instead of 4-bromobenzaldehyde.

Yellow solid, mp 177.9-178.3° C. (11.6 mg, 28%); IR (ATR) v=3006, 2922, 2852, 1629, 1560, 1434, 1355, 744 cm$^{-1}$; $^1$H NMR (400 MHz, CDCl$_3$) δ 8.84 (d, J=4.4 Hz, 1H), 8.40 (d, J=8.0 Hz, 1H), 8.25 (d, J=8.0 Hz, 1H), 8.12 (d, J=7.2 Hz, 1H), 8.07 (d, J=7.2 Hz, 1H), 8.02 (t, J=7.2 Hz, 1H), 7.70 (t, J=7.6 Hz, 1H), 7.67-7.60 (m, 2H), 7.52 (t, J=6.0 Hz, 1H), 7.31 (s, 1H), 7.07 (t, J=7.6 Hz, 1H), 6.49 (t, J=6.8 Hz, 1H); $^{13}$C NMR (100 MHz, CDCl$_3$) δ 158.5, 149.2, 147.0, 143.0, 139.2, 137.9, 132.4, 129.7, 128.1, 127.6, 126.2, 125.3, 124.2, 123.72, 123.66, 122.9, 121.1, 119.2, 109.7, 92.4; HRMS (ESI) calcd for $C_{20}H_{14}N_3$ 296.1182 ([M+H]$^+$). found 296.1182.

Example 15

6-(5-Chlorothiophen-2-yl)indolizino[3,2-c]quinoline

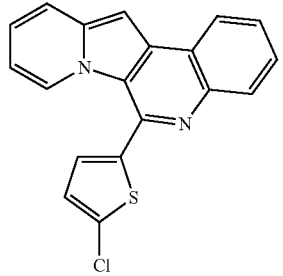 [SMILES: Clc1ccc(-c2nc3ccccc3c3cc4ccccn4c23)s1]

The target compound is obtained in the same manner as Example 1, except that 5-chlorothiphen-2-carbaldehyde is used instead of 4-bromobenzaldehyde.

Yellow solid, mp 161.4-161.7° C. (36.6 mg, 78%); IR (ATR) v=3041, 2937, 1632, 1561, 1493, 1352, 751 cm$^{-1}$; $^1$H NMR (400 MHz, CDCl$_3$) δ 8.34 (d, J=8.0 Hz, 2H), 8.21 (d, J=8.0 Hz, 1H), 7.69 (td, J=1.2, 6.8 Hz, 1H), 7.66-7.59 (m 2H), 7.26 (s, 1H), 7.19 (d, J=4.0 Hz, 1H), 7.11-7.04 (m, 2H), 6.57 (td, J=1.2, 6.4 Hz, 1H); $^{13}$C NMR (100 MHz, CDCl$_3$) δ 142.9, 140.5, 139.8, 139.2, 132.7, 132.1, 129.7, 127.8, 127.4, 126.82, 126.75, 126.3, 123.8, 123.6, 122.6, 121.2, 119.5, 110.2, 92.5; HRMS (ESI) calcd for $C_{19}H_{12}ClN_2S$ 335.0404 ([M+H]$^+$). found 335.0402.

Example 16

6-(4-Bromophenyl)-1-methylindolizino[3,2-c]quinoline

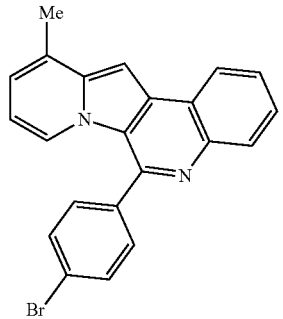 [SMILES: Cc1cccn2c1cc1c3ccccc3nc(-c3ccc(Br)cc3)c12]

The target compound is obtained in the same manner as Example 1, except that the compound obtained from Preparation Example 2.2 is used instead of the compound obtained from Preparation Example 2.1.

Yellow solid, mp 226.5-226.8° C. (45.0 mg, 83%); IR (ATR) v=3042, 2919, 1588, 1498, 1356 cm$^{-1}$; $^1$H NMR (400 MHz, CDCl$_3$) δ 8.42 (d, J=7.6 Hz, 1H), 8.23 (d, J=8.4 Hz, 1H), 7.80-7.72 (m, 3H), 7.70 (t, J=6.8 Hz, 1H), 7.64 (t, J=7.2 Hz, 1H), 7.57 (d, J=8.0 Hz, 2H), 7.29 (s, 1H), 6.89 (d, J=6.0 Hz, 1H), 6.43 (t, J=6.8 Hz, 1H), 2.61 (s, 3H); $^{13}$C NMR (100 MHz, CDCl$_3$) δ 147.4, 143.1, 140.1, 138.9, 132.5, 131.6, 130.7, 129.6, 128.3, 127.6, 125.9, 124.6, 123.58, 123.56, 122.6, 122.4, 110.2, 90.8, 18.8; HRMS (ESI) calcd for C$_{22}$H$_{16}$BrN$_2$ 387.0491 ([M+H]$^+$). found 387.0490.

Example 17

6-(3-Fluorophenyl)-11-methylindolizino[3,2-c]quinoline

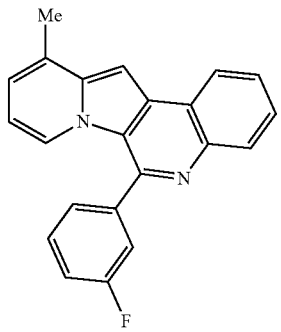 [SMILES: Cc1cccn2c1cc1c3ccccc3nc(-c3cccc(F)c3)c12]

The target compound is obtained in the same manner as Example 1, except that the compound obtained from Preparation Example 2.2 is used instead of the compound obtained from Preparation example 2.1, and 3-fluorobenzaldehyde is used instead of 4-bromobenzaldehyde.

Yellow solid, mp 176.1-176.5° C. (36.6 mg, 80%); IR (ATR) v=3042, 2903, 1561, 1496, 1364, 1110 cm$^{-1}$; $^1$H NMR (400 MHz, CDCl$_3$) δ 8.39 (d, J=8.0 Hz, 1H), 8.24 (d, J=8.0 Hz, 1H), 7.73-7.66 (m, 2H), 7.62 (t, J=7.2 Hz, 1H), 7.60-7.53 (m, 1H), 7.43 (d, J=8.8 Hz, 1H), 7.40 (d, J=8.8 Hz, 1H), 7.28 (dd, J=1.6, 8.4 Hz, 1H), 7.25 (s, 1H), 6.85 (d, J=6.8 Hz, 1H), 6.38 (t, J15=7.2 Hz, 1H), 2.58 (s, 3H); $^{13}$C NMR (100 MHz, CDCl$_3$) δ 163.3 (d, J$_{C,F}$=247.0 Hz), 147.2, 142.5 (d, J$_{C,F}$=287.0 Hz), 142.0 (d, J$_{C,F}$=8.0 Hz), 131.6, 131.02 (d, J$_{C,F}$=8.0 Hz), 129.6, 128.3, 127.6, 126.0, 124.7, 124.6, 124.5, 123.6, 122.6, 122.5, 121.4, 116.3 (d, J$_{C,F}$=6.0 Hz), 116.1 (d, J$_{C,F}$=7.0 Hz), 110.2, 90.8, 18.8; HRMS (ESI) calcd for C$_{22}$H$_{16}$FN$_2$ 327.1292 ([M+H]$^+$). found 327.1292.

Example 18

11-Methyl-6-(4-nitrophenyl)indolizino[3,2-c]quinoline

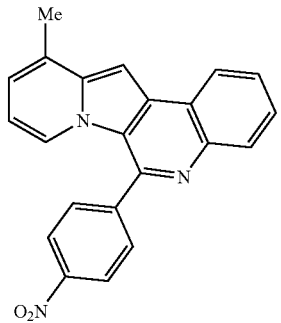 [SMILES: Cc1cccn2c1cc1c3ccccc3nc(-c3ccc([N+](=O)[O-])cc3)c12]

The target compound is obtained in the same manner as Example 1, except that the compound obtained from Preparation Example 2.2 is used instead of the compound obtained from Preparation Example 2.1, and 4-nitrobenzaldehyde is used instead of 4-bromobenzaldehyde.

Yellow solid, mp 259.7-260.4° C. (35.1 mg, 71%); IR (ATR) v=3026, 2920, 1631, 1595, 1441, 1341, 1381, 1102 cm$^{-1}$; $^1$H NMR (400 MHz, CDCl$_3$) δ 8.48 (d, J=6.8 Hz, 2H), 8.43 (d, J=7.6 Hz, 1H), 8.23 (d, J=8.0 Hz, 1H), 7.90 (d, J=6.8 Hz, 2H), 7.75-7.61 (m, 3H), 7.31 (s, 1H), 6.91 (d, J=6.4 Hz, 1H), 6.44 (t, J=6.8 Hz, 1H), 2.62 (s, 3H): $^{13}$C NMR (100 MHz, CDCl$_3$) δ 148.4, 146.4, 146.1, 143.0, 140.3, 131.8, 130.3, 129.7, 128.7, 127.9, 126.4, 124.5, 124.3, 123.7, 122.69, 122.67, 121.2, 110.6, 91.2, 18.8; HRMS (ESI) calcd for C$_{22}$H$_{16}$N$_3$O$_2$ 354.1237 ([M+H]$^+$). found 354.1235.

Example 19

6-(3-Methoxyphenyl)-11-methylindolizino[3,2-c]quinoline

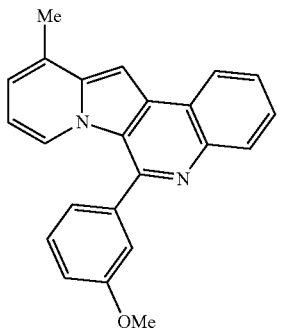 [SMILES: COc1cccc(-c2nc3ccccc3c3cc4c(C)cccn4c23)c1]

The target compound is obtained in the same manner as Example 1, except that the compound obtained from Preparation Example 2.2 is used instead of the compound obtained from Preparation Example 2.1, and 3-methoxybenzaldehyde is used instead of 4-bromobenzaldehyde.

Yellow solid, mp 165.0-166.0° C. (43.1 mg, 91%); IR (ATR) v=3119, 2922, 1588, 1485, 1364, 1255, 1039 cm$^{-1}$; $^1$H NMR (400 MHz, CDCl$_3$) δ 8.41 (d, J=8.0 Hz, 1H), 8.29 (d, J=8.4 Hz, 1H), 7.73 (d, J=7.2 Hz, 1H), 7.69 (d, J=8.0 Hz, 1H), 7.64 (t, J=7.6 Hz, 1H), 7.51 (t, J=7.6 Hz, 1H), 7.28 (s, 1H), 7.24-7.17 (m, 2H), 7.12 (d, J=8.0 Hz, 1H), 6.88 (d, J=6.4 Hz, 1H), 6.39 (d, J=7.2 Hz, 1H), 3.87 (s, 3H), 2.60 (s, 3H); $^{13}$C NMR (100 MHz, CDCl$_3$) δ 160.4, 148.6, 143.0, 141.1, 140.1, 131.4, 130.5, 129.6, 128.1, 127.6, 125.8, 124.9, 123.6, 122.6, 122.4, 121.0, 119.2, 115.6, 113.6, 110.0, 90.7, 55.6, 18.8; HRMS (ESI) calcd for C$_{23}$H$_{19}$N$_2$O 339.1492 ([M+H]$^+$). found 339.1493.

Example 20

11-Methyl-6-(p-tolyl)indolizino[3,2-c]quinoline

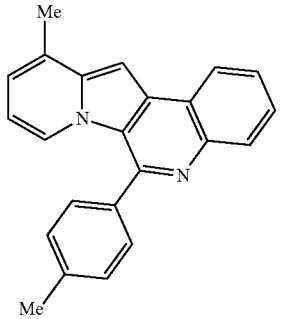

The target compound is obtained in the same manner as Example 1, except that the compound obtained from Preparation Example 2.2 is used instead of the compound obtained from Preparation Example 2.1, and 4-methylbenzaldehyde is used instead of 4-bromobenzaldehyde.

Yellow solid, mp 162.5-163.1° C. (35.7 mg, 79%); IR (ATR) v=3013, 2918, 1626, 1491, 1435, 1349 cm$^{-1}$; $^1$H NMR (400 MHz, CDCl$_3$) δ 8.40 (d, J=8.0 Hz, 1H), 8.25 (d, J=8.4 Hz, 1H), 7.79 (d, J=7.2 Hz, 1H), 7.68 (t, J=8.4 Hz, 1H), 7.62 (t, J=7.2 Hz, 1H), 7.55 (d, J=8.0 Hz, 2H), 7.40 (d, J=8.0 Hz, 2H), 6.87-6.81 (m, 1H), 6.36 (t, J=7.2 Hz, 1H), 2.59 (s, 3H), 2.51 (s, 3H); $^{13}$C NMR (100 MHz, CDCl$_3$) δ 149.1, 143.2, 140.0, 139.0, 137.1, 131.4, 130.0, 129.7, 128.7, 128.1, 127.4, 125.6, 124.9, 123.5, 122.6, 122.2, 121.8, 109.8, 90.6, 21.7, 18.8; HRMS (ESI) calcd for C$_{23}$H$_{19}$N$_2$ 323.1543 ([M+H]$^+$). found 323.1542.

Example 21

6-(3,5-Dimethoxyphenyl)-11-methylindolizino[3,2-c]quinoline

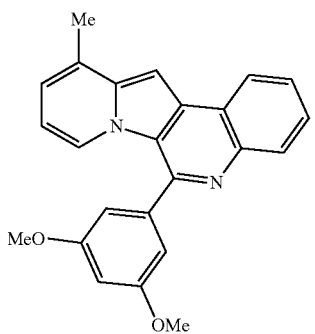 [SMILES: COc1cc(OC)cc(-c2nc3ccccc3c3cc4c(C)cccn4c23)c1]

The target compound is obtained in the same manner as Example 1, except that the compound obtained from Preparation Example 2.2 is used instead of the compound obtained from Preparation Example 2.1, and 3,5-dimethoxybenzaldehyde is used instead of 4-bromobenzaldehyde.

Yellow solid, mp 185.8-186.4° C. (39.7 mg, 77%); IR (ATR) v=2933, 2836, 1596, 1495, 1453, 1365, 1193, 1149 cm$^{-1}$; $^1$H NMR (400 MHz, CDCl$_3$) δ 8.40 (d, J=7.6 Hz, 1H), 8.26 (d, J=8.4 Hz, 1H), 7.77 (d, J=6.8 Hz, 1H), 7.69 (t, J=6.8 Hz, 1H), 7.62 (t, J=8.0 Hz, 1H), 7.62 (s, 1H), 6.86 (d, J=5.2 Hz, 1H), 6.78 (s, 2H), 6.66 (s, 1H), 6.41 (t, J=7.2 Hz, 1H), 3.83 (s, 6H), 2.58 (s, 3H); $^{13}$C NMR (100 MHz, CDCl$_3$) δ 161.6, 148.6, 143.0, 141.7, 140.0, 131.4, 129.7, 128.0, 127.5, 125.8, 125.0, 123.6, 122.6, 122.4, 121.4, 110.1, 106.4, 101.9, 90.6, 55.7, 18.8; HRMS (ESI) calcd for C$_{24}$H$_{21}$N$_2$O$_2$ 369.1598 ([M+H]$^+$). found 369.1595.

Example 22

6-(3,4-Dimethoxyphenyl)-11-methylindolizino[3,2-c]quinoline

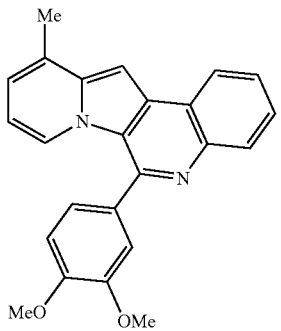 [SMILES: COc1ccc(-c2nc3ccccc3c3cc4c(C)cccn4c23)cc1OC]

The target compound is obtained in the same manner as Example 1, except that the compound obtained from Preparation Example 2.2 is used instead of the compound obtained from Preparation Example 2.1, and 3,4-dimethoxybenzaldehyde is used instead of 4-bromobenzaldehyde.

Yellow solid, mp 162.8-163.3° C. (35.1 mg, 68%); IR (ATR) v=2919, 2845, 1602, 1492, 1411, 1365, 1138 cm$^{-1}$; $^1$H NMR (400 MHz, CDCl$_3$) δ 8.40 (d, J=7.6 Hz, 1H), 8.25 (d, J=8.0 Hz, 1H), 7.79 (d, J=7.2 Hz, 1H), 7.69 (t, J=7.2 Hz, 1H), 7.62 (t, J=7.6 Hz, 1H), 7.27 (s, 1H), 7.22 (d, J=8.0 Hz, 1H), 7.19 (s, 1H), 7.09 (d, J=8.0 Hz, 1H), 6.86 (d, J=6.4 Hz, 1H), 6.39 (d, J=7.2 Hz, 1H), 4.01 (s, 3H), 3.90 (s, 3H), 2.59 (s, 3H); $^{13}$C NMR (100 MHz. CDCl$_3$) δ 149.8, 149.6, 148.6, 143.1, 140.0, 132.4, 131.4, 129.6, 128.1, 127.5, 125.7, 124.9, 123.5, 122.6, 122.3, 121.8, 121.3, 111.9, 111.8, 109.9, 90.7, 56.2, 56.1, 18.8; HRMS (ESI) calcd for C$_{24}$H$_{21}$N$_2$O$_2$ 369.1598 ([M+H]$^+$). found 369.1595.

Example 23

6-(Furan-2-yl)-11-methylindolizino[3,2-c]quinoline

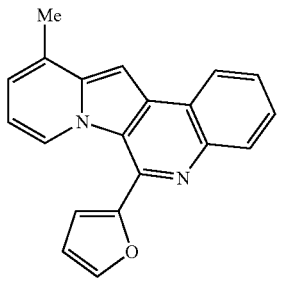 [SMILES: Cc1cccn2c1cc1c3ccccc3nc(-c3ccco3)c12]

The target compound is obtained in the same manner as Example 1, except that the compound obtained from Preparation Example 2.2 is used instead of the compound obtained from Preparation Example 2.1, and furan-2-carbaldehyde is used instead of 4-bromobenzaldehyde.

Yellow solid, mp 112.4-113.2° C. (33.0 mg, 79%); IR (ATR) v=3096, 2922, 1611, 1481, 1438, 1365, 1013 cm$^{-1}$; $^1$H NMR (400 MHz, CDCl$_3$) δ 8.35 (d, J=6.4 Hz, 1H), 8.25 (d, J=8.4 Hz, 1H), 7.84 (d, J=6.8 Hz, 1H), 7.72 (s, 1H), 7.68 (t, J=6.8 Hz, 1H), 7.61 (t, J=7.2 Hz, 1H), 7.24-7.17 (m, 1H), 7.03 (d, J=3.2 Hz, 1H), 6.87 (s, 1H), 6.72 (s, 1H), 6.54-6.46 (m, 1H), 2.56 (s, 3H); $^{13}$C NMR (100 MHz, CDCl$_3$) δ 151.7, 143.2, 143.1, 140.1, 138.5, 131.7, 129.8, 128.0, 127.6, 126.2, 125.0, 123.6, 122.9, 122.5, 122.0, 112.3, 111.5, 110.2, 90.8, 18.8; HRMS (ESI) calcd for C$_{20}$H$_{15}$N$_2$O 299.1179 ([M+H]$^+$). found 299.1178.

Example 24

9-Bromo-6-(4-methoxyphenyl)indolizino[3,2-c]quinoline

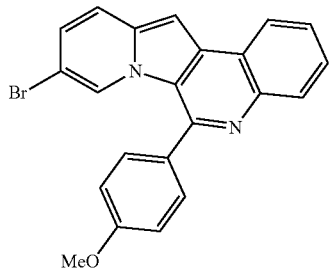 [SMILES: COc1ccc(-c2nc3ccccc3c3cc4ccc(Br)cn4c23)cc1]

The target compound is obtained in the same manner as Example 1, except that the compound obtained from Preparation Example 2.3 is used instead of the compound obtained from Preparation Example 2.1, and furan-2-carbaldehyde is used instead of 4-bromobenzaldehyde.

Yellow solid, mp 229.5-230.0° C. (50.2 mg, 89%); IR (ATR) v=3057, 3003, 1606, 1489, 1435, 1381, 1242, 1173, 669 cm$^{-1}$; $^1$H NMR (400 MHz, CDCl$_3$) δ 8.33 (d, J=7.6 Hz, 1H), 8.24 (d, J=8.4 Hz, 1H), 8.05 (s, 1H), 7.69 (t, J=7.6 Hz, 1H), 7.64-7.57 (m, 3H), 7.51 (d, J=9.2 Hz, 1H), 7.28 (s, 1H), 7.16 (d, J=8.4 Hz, 2H), 7.06 (d, J=9.6 Hz, 1H), 3.94 (s, 3H); $^{13}$C NMR (100 MHz, CDCl$_3$) δ 160.8, 148.5, 143.2, 136.7, 131.7, 131.5, 130.1, 129.7, 127.8, 127.0, 126.5, 126.0, 123.6, 122.3, 121.4, 119.9, 114.9, 104.2, 93.4, 55.7; HRMS (ESI) calcd for C$_{22}$H$_{16}$BrN$_2$O 403.0441 ([M+H]$^+$). found 403.0437.

Example 25

9-Bromo-6-(p-tolyl)indolizino[3,2-c]quinolone

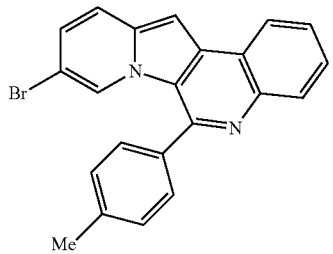 [SMILES: Cc1ccc(-c2nc3ccccc3c3cc4ccc(Br)cn4c23)cc1]

The target compound is obtained in the same manner as Example 1, except that the compound obtained from Preparation Example 2.3 is used instead of the compound obtained from Preparation Example 2.1, and 4-methylbenzaldehyde is used instead of 4-bromobenzaldehyde.

Yellow solid, mp 230.8-231.2° C. (23.9 mg, 44%); IR (ATR) v=2921, 2852, 1610, 1487, 1435, 667 cm$^{-1}$; $^1$H NMR (400 MHz. CDCl$_3$) δ 8.33 (d, J=7.6 Hz, 1H), 8.25 (d, J=8.4 Hz, 1H), 7.96 (s, 1H), 7.69 (t, J=7.2 Hz, 1H), 7.61 (t, J=7.2 Hz, 1H), 7.55 (d, J=7.6 Hz, 2H), 7.50 (d, J=9.6 Hz, 1H), 7.44 (d, J=8.0 Hz, 2H), 7.27 (s, 1H), 7.05 (d, J=9.6 Hz, 1H), 2.52 (s, 3H); $^{13}$C NMR (100 MHz, CDCl$_3$) δ 148.9, 143.2, 139.6, 136.7, 136.2, 131.6, 130.1, 129.8, 128.5, 127.8, 127.0, 126.5, 126.0, 123.6, 122.3, 121.3, 119.8, 104.2, 93.4, 21.7; HRMS (ESI) calcd for C$_{22}$H$_{16}$BrN$_2$ 387.0491 ([M+H]$^+$). found 387.0490.

Example 26

9-Bromo-6-(3,4-dimethoxyphenyl)indolizino[3,2-c]quinoline

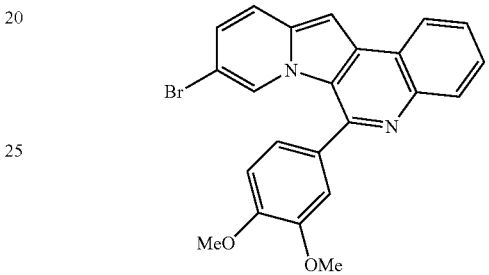

The target compound is obtained in the same manner as Example 1, except that the compound obtained from Preparation Example 2.3 is used instead of the compound obtained from Preparation Example 2.1, and 3,4-dimethoxybenzaldehyde is used instead of 4-bromobenzaldehyde.

Green solid, mp 188.5-189.0° C. (45.5 mg, 75%); IR (ATR) v=3103, 3000, 1600, 1490, 1460, 1372, 1132, 667 cm$^{-1}$; $^1$H NMR (400 MHz, CDCl$_3$) δ 8.34 (d, J=8.0 Hz, 1H), 8.27 (d, J=8.0 Hz, 1H), 8.10 (s, 1H), 7.70 (t, J=7.2 Hz, 1H), 7.63 (t, J=7.2 Hz, 1H), 7.54 (d, J=9.6 Hz, 1H), 7.31 (s, 1H), 7.26-7.19 (m, 2H), 7.12 (d, J=8.0 Hz, 1H), 7.09 (d, J=9.6 Hz, 1H), 4.02 (s, 3H), 3.92 (s, 3H); $^{13}$C NMR (100 MHz, CDCl$_3$) δ 150.3, 149.9, 148.3, 143.0, 136.9, 131.8, 131.4, 129.5, 128.0, 127.1, 126.7, 126.1, 123.6, 122.3, 121.4, 121.2, 119.9, 111.9, 111.8, 104.3, 93.5, 56.4, 56.3; HRMS (ESI) calcd for C$_{23}$H$_{18}$BrN$_2$O$_2$ 433.0546 ([M+H]$^+$). found 433.0543.

Example 27

9-Bromo-6-(4naphthalen-1-yl)indolizino[3,2-c]quinoline

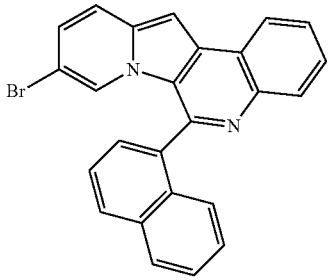 [SMILES: Brc1ccc2cc3c4ccccc4nc(-c4cccc5ccccc45)c3n2c1]

The target compound is obtained in the same manner as Example 1, except that the compound obtained from Preparation Example 2.3 is used instead of the compound obtained from Preparation Example 2.1, and 1-naphthaldehyde is used instead of 4-bromobenzaldehyde.

Yellow solid, mp 212.0-212.7° C. (49.2 mg, 83%); IR (ATR) v=3051, 2922, 1618, 1491, 669 cm$^{-1}$; $^1$H NMR (400 MHz, CDCl$_3$) δ 8.43 (d, J=8.0 Hz, 1H), 8.31 (d, J=8.0 Hz, 1H), 8.16-8.09 (m, 1H), 8.02 (d, J=8.0 Hz, 1H), 7.79-7.65 (m, 4H), 7.54 (d, J=7.2 Hz, 1H), 7.50 (d, J=9.6 Hz, 1H), 7.39 (d, J=8.4 Hz, 1H), 7.35 (s, 1H), 7.32 (t, J=7.2 Hz, 1H), 7.21 (s, 1H), 6.98 (d, J=9.2 Hz, 1H); $^{13}$C NMR (100 MHz, CDCl$_3$) δ 147.5, 143.4, 136.8, 136.1, 134.0, 131.5, 131.4, 130.0, 129.9, 128.7, 128.0, 127.4, 126.9, 126.78, 126.76, 126.6, 126.3, 126.1, 125.0, 123.7, 122.6, 122.2, 119.7, 104.5, 93.3; HRMS (ESI) calcd for C$_{25}$H$_{16}$BrN$_2$ 423.0491 ([M+H]$^+$). found 423.0487.

Example 28

9-Bromo-6-(5-bromothiophen-2-yl)indolizino[3,2-c]quinoline

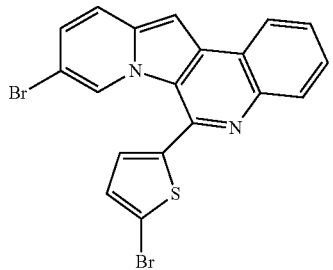 [SMILES: Brc1ccc2cc3c4ccccc4nc(-c4ccc(Br)s4)c3n2c1]

The target compound is obtained in the same manner as Example 1, except that the compound obtained from Preparation Example 2.3 is used instead of the compound obtained from Preparation Example 2.1, and 5-bromothiophen-2-carbaldehyde is used instead of 4-bromobenzaldehyde.

Yellow solid, mp 223.3-223.7° C. (37.2 mg, 58%); IR (ATR) v=3059, 3013, 1618, 1561, 1490, 1420, 665 cm$^{-1}$; $^1$H NMR (400 MHz, CDCl$_3$) δ 8.48 (s, 1H), 8.32 (d, J=8.0 Hz, 1H), 8.22 (d, J=8.4 Hz, 1H), 7.71 (t, J=7.2 Hz, 1H), 7.64 (t, J=7.2 Hz, 1H), 7.56 (d, J=9.2 Hz, 1H), 7.30 (s, 1H), 7.26 (s, 1H), 7.20 (d, J=3.6 Hz, 1H), 7.14 (d, J=9.2 Hz, 1H); $^{13}$C NMR (100 MHz, CDCl$_3$) δ 142.8, 142.0, 140.5, 137.1, 132.2, 130.5, 129.7, 128.6, 128.2, 127.1, 126.79, 126.75, 123.6, 122.5, 121.0, 120.1, 117.3, 115.7, 104.8, 93.8; HRMS (ESI) calcd for C$_{19}$H$_{11}$Br$_2$N$_2$S 456.9004 ([M+H]$^+$). found 456.8998.

Example 29

9-Bromo-6-(furna-2-yl)indolizino[3,2-c]quinoline

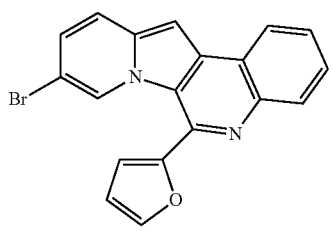 [SMILES: Brc1ccc2cc3c4ccccc4nc(-c4ccco4)c3n2c1]

The target compound is obtained in the same manner as Example 1, except that the compound obtained from Preparation Example 2.3 is used instead of the compound obtained from Preparation Example 2.1, and furan-2-carbaldehyde is used instead of 4-bromobenzaldehyde.

Yellow solid, mp 193.3-193.6° C. (47.3 mg, 93%); IR (ATR) v=3065, 3013, 1599, 1480, 1313, 668 cm$^{-1}$; $^1$H NMR (400 MHz, CDCl$_3$) δ 8.30 (d, J=7.6 Hz, 1H), 8.25 (d, J=8.4 Hz, 1H), 8.09 (s, 1H), 7.78 (s, 1H), 7.70 (t, J=7.6 Hz, 1H), 7.63 (t, J=7.2 Hz, 1H), 7.52 (d, J=9.2 Hz, 1H), 7.26 (s, 1H), 7.15-7.06 (m, 2H), 6.78 (s, 1H); $^{13}$C NMR (100 MHz, CDCl$_3$) δ 143.4, 142.9, 138.2, 137.0, 132.1, 129.8, 128.0, 127.6, 126.9, 126.6, 123.6, 122.6, 121.4, 119.8, 112.7, 112.2, 104.8, 93.6; HRMS (ESI) calcd for C$_{19}$H$_{12}$BrN$_2$O 363.0128 ([M+H]$^+$). found 363.0126.

Example 30

Methyl 6-(4-bromophenyl)indolizino[3,2-c]quinoline-12-carboxylate

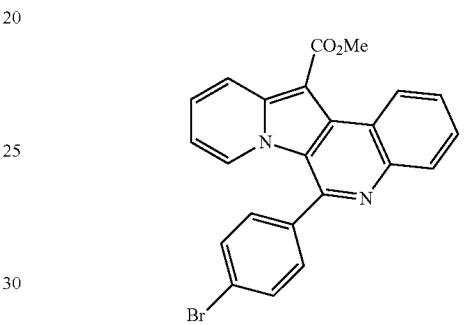

The target compound is obtained in the same manner as Example 1, except that the compound obtained from Preparation Example 2.4 is used instead of the compound obtained from Preparation Example 2.1.

Yellow solid, mp 232.3-232.5° C. (46.5 mg, 77%); IR (ATR) v=3240, 2851, 1679, 1631, 1489, 1427, 1350, 1135, 655 cm$^{-1}$; $^1$H NMR (400 MHz, CDCl$_3$) δ 9.66 (d, J=8.4 Hz, 1H), 8.48 (d, J=9.2 Hz, 1H), 8.23 (d, J=8.4 Hz, 1H), 7.98 (d, J=7.2 Hz, 1H), 7.80-7.72 (m, 3H), 7.68 (t, J=7.2 Hz, 1H), 7.53 (d, J=8.0 Hz, 2H), 7.36 (d, J=7.6 Hz, 1H), 6.68 (t, J=7.2 Hz, 1H), 4.12 (s, 3H); $^{13}$C NMR (100 MHz, CDCl$_3$) δ 165.9, 146.8, 144.7, 141.6, 138.7, 132.9, 131.2, 130.5, 129.8, 128.7, 127.64, 127.61, 127.2, 126.2, 123.9, 122.4, 121.9, 120.9, 112.4, 99.6, 51.7; HRMS (ESI) calcd for C$_{22}$H$_{16}$BrN$_2$O$_2$ 431.0390 ([M+H]$^+$). found 431.0388.

Example 31

Methyl 6-(3,5-dimethoxyphenyl)indolizino[3,2-c]quinoline-12-carboxylate

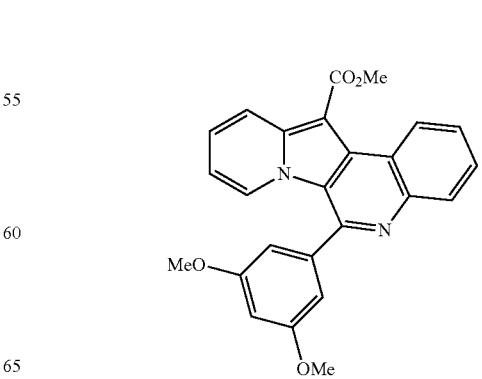

The target compound is obtained in the same manner as Example 1, except that the compound obtained from Preparation Example 2.4 is used instead of the compound obtained from Preparation Example 2.1, and 3,5-dimethoxybenzaldehyde is used instead of 4-bromobenzaldehyde.

Yellow solid, mp 205.9-206.3° C. (53.7 mg, 93%); IR (ATR) v=2936, 2839, 1690, 1598, 1492, 1352, 1134 cm$^{-1}$; $^1$H NMR (400 MHz, CDCl$_3$) δ 9.68 (d, J=8.0 Hz, 1H), 8.46 (d, J=9.2 Hz, 1H), 8.26 (d, J=8.0 Hz, 1H), 7.96 (d, J=7.2 Hz, 1H), 7.74 (t, J=7.2 Hz, 1H), 7.66 (t, J=8.0 Hz, 1H), 7.34 (t, J=7.6 Hz, 1H), 6.74 (s, 2H), 6.70-6.60 (m, 2H), 4.10 (s, 3H), 3.84 (s, 6H); $^{13}$C NMR (100 MHz, CDCl$_3$) δ 165.9, 161.9, 147.9, 144.5, 141.6, 141.4, 131.0, 129.8, 128.5, 127.7, 127.64, 127.57, 126.0, 122.4, 121.9, 120.5, 112.3, 106.2, 102.0, 99.4, 55.8, 51.6; HRMS (ESI) calcd for C$_{25}$H$_{21}$N$_2$O$_4$ 413.1496 ([M+H]$^+$). found 413.1506.

Example 32

Methyl 6-(naphthalene-1-yl)indolizino[3,2-c]quinoline-12-carboxylate

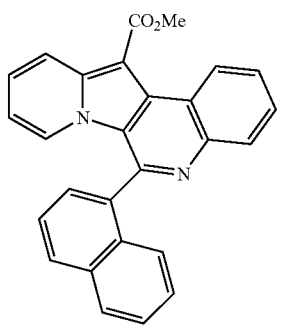 [SMILES: COC(=O)c1c2c3ccccc3nc(-c3cccc4ccccc34)c2n2ccccc12]

The target compound is obtained in the same manner as Example 1, except that the compound obtained from Preparation Example 2.4 is used instead of the compound obtained from Preparation Example 2.1, and 1-naphthaldehyde is used instead of 4-bromobenzaldehyde.

Yellow solid, mp 245.8-246.2° C. (55.8 mg, 99%); IR (ATR) v=3048, 2985, 1697, 1490, 1437, 1350, 1133 cm$^{-1}$; $^1$H NMR (400 MHz, CDCl$_3$) δ 9.76 (d, J=8.0 Hz, 1H), 8.43 (d, J=9.2 Hz, 1H), 8.30 (d, J=8.0 Hz, 1H), 7.59 (dd, J=2.8, 6.8 Hz, 1H), 7.98 (d, J=8.4 Hz, 1H), 7.77 (t, J=7.2 Hz, 1H), 7.74-7.66 (m, 3H), 7.49 (t, J=6.8 Hz, 1H), 7.34 (d, J=7.2 Hz, 1H), 7.31 (d, J=8.4 Hz, 1H), 7.26 (dd, J=6.8, 7.2 Hz, 1H), 7.22 (dd, J=6.8, 9.2 Hz, 1H), 6.32 (t, J=6.8 Hz, 1H), 4.11 (s, 3H); $^{13}$C NMR (100 MHz, CDCl$_3$) δ 166.0, 146.8, 145.0, 141.5, 136.7, 134.0, 131.4, 130.8, 129.9, 129.8, 128.6, 128.5, 127.7, 127.5, 127.4, 126.94, 126.87, 126.8, 126.2, 126.1, 124.9, 123.2, 122.5, 120.4, 112.4, 99.3, 51.6; HRMS (ESI) calcd for C$_2$H$_{19}$N$_2$O$_2$ 403.1441 ([M+H]$^+$). found 403.1437.

Example 33

Methyl 6-(1H-pyrrol-2-yl)indolizino[3,2-c]quinoline-12-carboxylate

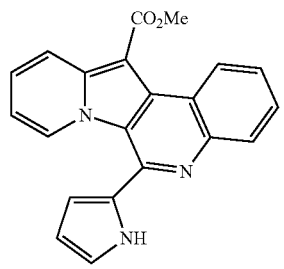 [SMILES: COC(=O)c1c2c3ccccc3nc(-c3ccc[nH]3)c2n2ccccc12]

The target compound is obtained in the same manner as Example 1, except that the compound obtained from Preparation Example 2.4 is used instead of the compound obtained from Preparation Example 2.1, and 1H-pyrrole-2-carbaldehyde is used instead of 4-bromobenzaldehyde.

Yellow solid, mp 230.8-231.4° C. (42.1 mg, 88%); IR (ATR) v=3323, 3108, 2944, 1690, 1588, 1494, 1439, 1350, 1224 cm$^{-1}$; $^1$H NMR (400 MHz, CDCl$_3$) δ 10.06 (s, 1H), 9.46 (d, J=8.0 Hz, 1H), 8.65-8.53 (m, 1H), 8.35 (d, J=9.2 Hz, 1H), 7.98 (d, J=8.0 Hz, 1H), 7.54-7.40 (m, 2H), 7.32 (t, J=6.8 Hz, 1H), 7.08 (s, 1H), 6.70 (t, J=6.8 Hz, 1H), 6.60 (s, 1H), 6.41 (s, 1H), 4.09 (s, 3H); $^{13}$C NMR (100 MHz, CDCl$_3$) δ 165.9, 144.3, 141.5, 140.4, 131.3, 128.7, 128.5, 128.3, 127.8, 127.6, 127.5, 125.4, 121.9, 121.8, 120.5, 120.3, 111.8, 110.9, 110.0, 99.2, 51.6; HRMS (ESI) calcd for C$_{21}$H$_{16}$N$_3$O$_2$ 342.1237 ([M+H]$^+$). found 342.1229.

Example 34

Ethyl 6-(3-fluorophenyl)indolizino[3,2-c]quinoline-12-carboxylate

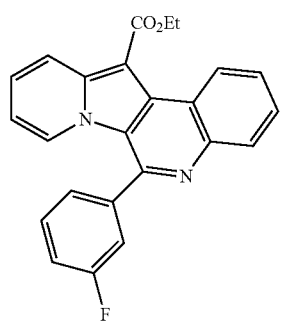 [SMILES: CCOC(=O)c1c2c3ccccc3nc(-c3cccc(F)c3)c2n2ccccc12]

The target compound is obtained in the same manner as Example 1, except that the compound obtained from Preparation Example 2.5 is used instead of the compound obtained from Preparation Example 2.1, and 3-fluorobenzaldehyde is used instead of 4-bromobenzaldehyde.

Yellow solid, mp 202.1-202.4° C. (53.8 mg, 100%); IR (ATR) v=3055, 3033, 2980, 1676, 1613, 1490, 1434, 1372, 1135 cm$^{-1}$; $^1$H NMR (400 MHz, CDCl$_3$) δ 9.68 (d, J=8.4 Hz, 1H), 8.49 (d, J=8.8 Hz, 1H), 8.24 (d, J=8.0 Hz, 1H), 7.89 (d, J=6.4 Hz, 1H), 7.75 (t, J=6.8 Hz, 1H), 7.67 (t, J=7.6 Hz, 1H), 7.63-7.54 (m, 1H), 7.44-7.25 (m, 4H), 6.68-6.54 (m, 1H), 4.59 (q, J=7.2 Hz, 2H), 1.56 (t, J=7.2 Hz, 3H); $^{13}$C NMR (100 MHz, CDCl$_3$) δ 165.5, 163.4 (d, $J_{C,F}$=247.9 Hz), 146.6, 143.0 (d, $J_{C,F}$=295.8 Hz), 141.8 (d, $J_{C,F}$=7.5 Hz), 131.4 (d, $J_{C,F}$=33.2 Hz), 131.2, 129.8, 128.6, 127.6 (d, $J_{C,F}$=24.0 Hz), 127.2, 126.1, 124.6, 124.5, 122.4, 121.7, 120.7, 116.6 (d, $J_{C,F}$=20.9 Hz), 116.2, 116.0, 112.3, 99.8, 60.7, 14.8; HRMS (ESI) calcd for C$_{24}$H$_{18}$FN$_2$O$_2$ 385.1347 ([M+H]$^+$). found 385.1345.

Example 35

Ethyl 6-(3-fluorophenyl)indolizino[3,2-c]quinoline-12-carboxylate

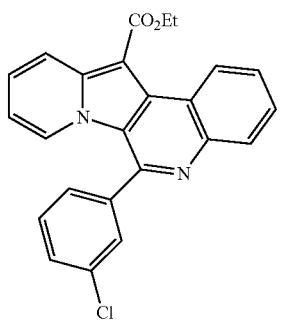 [SMILES: CCOC(=O)c1c2c3ccccc3nc(-c3cccc(Cl)c3)c2n2ccccc12]

The target compound is obtained in the same manner as Example 1, except that the compound obtained from Preparation Example 2.5 is used instead of the compound obtained from Preparation Example 2.1, and 3-chlorobenzaldehyde is used instead of 4-bromobenzaldehyde.

Yellow solid, mp 214.3-214.5° C. (53.3 mg, 95%); IR (ATR) v=3111, 2961, 1679, 1631, 1489, 1435, 1386, 1218, 1174, 1026, 741 cm$^{-1}$; $^1$H NMR (400 MHz, CDCl$_3$) δ 9.68 (d, J=8.4 Hz, 1H), 8.49 (d, J=8.8 Hz, 1H), 8.23 (d, J=8.0 Hz, 1H), 7.92 (d, J=6.4 Hz, 1H), 7.75 (t, J=7.2 Hz, 1H), 7.72-7.62 (m, 2H), 7.61-7.51 (m, 2H), 7.51-7.45 (m, 1H), 7.34 (t, J=7.2 Hz, 1H), 6.65 (t, J=6.8 Hz, 1H), 4.59 (q, J=7.2 Hz, 2H), 1.56 (t, J=7.2 Hz, 3H); $^{13}$C NMR (100 MHz, CDCl$_3$) δ 165.4, 146.4, 144.5, 141.6, 141.5, 135.7, 131.2, 130.9, 129.8, 129.7, 129.0, 128.6, 127.8, 127.5, 127.2, 126.9, 126.1, 122.4, 121.7, 120.8, 112.3, 99.9, 60.7, 14.8; HRMS (ESI) calcd for C$_{24}$H$_{18}$ClN$_2$O$_2$ 401.1051 ([M+H]$^+$). found 401.1048.

Example 36

Ethyl 6-(4-nitrophenyl)indolizino[3,2-c]quinoline-12-carboxylate

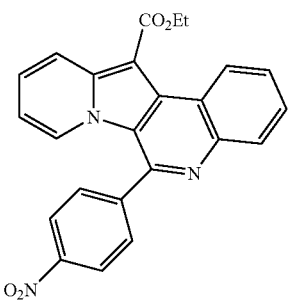 [SMILES: CCOC(=O)c1c2c3ccccc3nc(-c3ccc([N+](=O)[O-])cc3)c2n2ccccc12]

The target compound is obtained in the same manner as Example 1, except that the compound obtained from Preparation Example 2.5 is used instead of the compound obtained from Preparation Example 2.1, and 4-nitrobenzaldehyde is used instead of 4-bromobenzaldehyde.

Yellow solid, mp 245.8-246.1° C. (43.2 mg, 75%); IR (ATR) v=3112, 2985, 1689, 1597, 1560, 1436, 1349, 1215, 1137 cm$^{-1}$; $^1$H NMR (400 MHz, CDCl$_3$) δ 9.68 (d, J=8.4 Hz, 1H), 8.51 (d, J=9.6 Hz, 1H), 8.48 (d, J=8.8 Hz, 2H), 8.21 (d, J=8.0 Hz, 1H), 7.90-7.82 (m, 3H), 7.75 (t, J=7.2 Hz, 1H), 7.68 (t, J=7.2 Hz, 1H), 7.37 (dd, J=6.8, 8.8 Hz, 1H), 6.67 (t, J=6.4 Hz, 1H), 4.60 (q, J=7.2 Hz, 2H), 1.57 (t, J=7.2 Hz, 3H); $^{13}$C NMR (100 MHz, CDCl$_3$) δ 165.3, 148.5, 146.1, 145.4, 144.5, 141.6, 131.3, 130.2, 129.8, 128.8, 127.8, 127.7, 126.8, 126.5, 124.7, 122.4, 121.4, 121.0, 112.5, 100.1, 60.8, 14.8; HRMS (ESI) calcd for C$_{24}$H$_{18}$N$_3$O$_4$ 412.1292 ([M+H]$^+$). found 412.1286.

Example 37

Ethyl 6-(3-methoxyphenyl)indolizino[3,2-c]quinoline-12-carboxylate

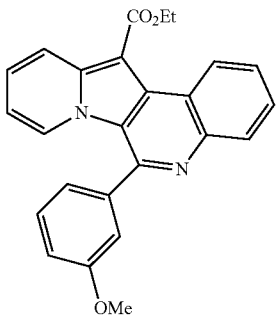 [SMILES: CCOC(=O)c1c2c3ccccc3nc(-c3cccc(OC)c3)c2n2ccccc12]

The target compound is obtained in the same manner as Example 1, except that the compound obtained from Preparation Example 2.5 is used instead of the compound obtained from Preparation Example 2.1, and 3-methoxybenzaldehyde is used instead of 4-bromobenzaldehyde.

Yellow solid, mp 173.4-173.8° C. (51.6 mg, 93%); IR (ATR) v=3031, 2957, 1675, 1588, 1488, 1434, 1350, 1109 cm$^{-1}$; $^1$H NMR (400 MHz, CDCl$_3$) δ 9.69 (d, J=8.4 Hz, 1H), 8.49 (d, J=9.2 Hz, 1H), 8.27 (d, J=8.0 Hz, 1H), 7.92 (d, J=7.2 Hz, 1H), 7.75 (t, J=7.2 Hz, 1H), 7.66 (t, J=6.8 Hz, 1H), 7.52 (t, J=8.0 Hz, 1H), 7.33 (t, J=6.8 Hz, 1H), 7.20-7.08 (m, 3H), 6.62 (t, J=6.8 Hz, 1H), 4.60 (q, J=7.2 Hz, 2H), 3.87 (s, 3H), 1.56 (t, J=7.2 Hz, 3H); $^{13}$C NMR (100 MHz, CDCl$_3$) δ 165.6, 160.6, 148.0, 144.6, 141.6, 140.9, 131.0, 130.9, 129.8, 128.5, 127.7, 127.54, 127.46, 125.9, 122.4, 122.0, 120.8, 120.6, 115.8, 113.5, 112.1, 99.7, 60.6, 55.6, 14.8; HRMS (ESI) calcd for C$_{25}$H$_{21}$N$_2$O$_3$ 397.1547 ([M+H]$^+$). found 397.1542.

Example 38

Ethyl 6-(3,4-dimethoxyphenyl)indolizino[3,2-c]quinoline-12-carboxylate

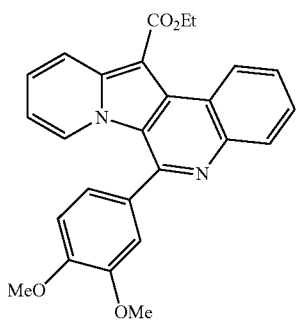 [SMILES: CCOC(=O)c1c2c3ccccc3nc(-c3ccc(OC)c(OC)c3)c2n2ccccc12]

The target compound is obtained in the same manner as Example 1, except that the compound obtained from Preparation Example 2.5 is used instead of the compound obtained from Preparation Example 2.1, and 3,4-dimethoxybenzaldehyde is used instead of 4-bromobenzaldehyde.

Yellow solid, mp 195.5-195.8° C. (58.5 mg, 98%); IR (ATR) v=3074, 2969, 1681, 1600, 1497, 1435, 1350, 1132, 1024 cm$^{-1}$; $^1$H NMR (400 MHz, CDCl$_3$) δ 9.68 (d, J=8.4 Hz, 1H), 8.49 (d, J=9.2 Hz, 1H), 8.25 (d, J=8.0 Hz, 1H), 7.98 (d, J=7.2 Hz, 1H), 7.73 (t, J=6.8 Hz, 1H), 7.65 (t, J=6.8 Hz, 1H), 7.33 (t, J=7.6 Hz, 1H), 7.20-7.12 (m, 2H), 7.09 (d, J=8.0 Hz, 1H), 6.64 (t, J=7.2 Hz, 1H), 4.59 (q, J=7.2 Hz, 2H), 4.01 (s, 3H), 3.91 (s, 3H), 1.56 (t, J=7.2 Hz, 3H); $^{13}$C NMR (100 MHz, CDCl$_3$) δ 165.5, 150.0, 149.9, 147.9, 144.6, 141.5, 132.1, 131.0, 129.6, 128.4, 127.7, 127.5, 127.4, 125.7, 122.3, 122.13, 122.14, 120.5, 112.1, 112.0, 111.5, 99.6, 60.6, 56.2, 56.2, 14.7; HRMS (ESI) calcd for C$_{26}$H$_{22}$N$_2$O$_4$ 427.1652 ([M+H]$^+$). found 427.1660.

Example 39

Ethyl 6-(naphthalene-2-yl)indolizino[3,2-c]quinoline-12-carboxylate

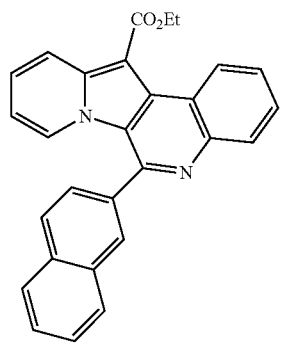 [SMILES: CCOC(=O)c1c2c3ccccc3nc(-c3ccc4ccccc4c3)c2n2ccccc12]

The target compound is obtained in the same manner as Example 1, except that the compound obtained from Preparation Example 2.5 is used instead of the compound obtained from Preparation Example 2.1, and 2-naphthaldehyde is used instead of 4-bromobenzaldehyde.

Yellow solid, mp 210.3-210.7° C. (58.3 mg, 100%); IR (ATR) v=3125, 2973, 1679, 1599, 1492, 1434, 1377, 1215, 1105, 1030 cm$^{-1}$; $^1$H NMR (400 MHz, CDCl$_3$) δ 9.71 (d, J=8.4 Hz, 1H), 8.49 (d, J=9.2 Hz, 1H), 8.28 (d, J=8.0 Hz, 1H), 8.18 (s, 1H), 8.07 (d, J=8.4 Hz, 1H), 7.98 (d, J=7.6 Hz, 1H), 7.96-7.90 (m, 2H), 7.75 (t, J=7.2 Hz, 1H), 7.70-7.64 (m, 2H), 7.64-7.54 (m, 2H), 7.29 (dd, J=6.8, 9.2 Hz, 1H), 6.49 (t, J=6.8 Hz, 1H), 4.61 (q, J=7.2 Hz, 2H), 1.57 (t, J=7.2 Hz, 3H); $^{13}$C NMR (100 MHz, CDCl$_3$) δ 165.6, 148.0, 144.7, 141.6, 137.0, 133.8, 133.6, 131.1, 129.8, 129.5, 128.7, 128.5, 128.2, 128.1, 127.8, 127.46, 127.44, 127.1, 127.0, 126.0, 125.9, 122.4, 122.2, 120.6, 112.1, 99.7, 60.6, 14.8; HRMS (ESI) calcd for C$_{28}$H$_{21}$N$_2$O$_2$ 417.1598 ([M+H]$^+$). found 417.1598.

Example 40

9-(3,5-Dimethoxyphenyl)-6-(4-methoxyphenyl)indolizino[3,2-c]quinoline

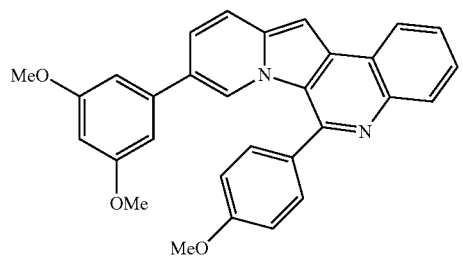 [SMILES: COc1ccc(-c2nc3ccccc3c3cc4ccc(-c5cc(OC)cc(OC)c5)cn4c23)cc1]

First, 0.07 mol of the compound obtained from Example 24, 0.0035 mmol (0.05 eq.) of Pd(PPh$_3$)$_4$, 0.077 mmol (1.1 eq.) of 3,5-dimethoxyphenylboronic acid and 0.21 mmol (3 eq.) of K$_3$PO$_4$ are dissolved into 1.5 ml of a mixed solvent containing toluene/methanol/water (1:1:1), and the reaction mixture is allowed to react at 120° C. for 4 hours. After the completion of the reaction, the reaction mixture is concentrated under reduced pressure. Then, the concentrated reaction mixture is dissolved by adding 3 ml of dichloromethane thereto and washed with 3 ml of water. The aqueous layer is extracted once more by adding 3 ml of dichloromethane thereto, and the organic layers are combined, dried over magnesium sulfate and concentrated under reduced pressure. The concentrated reaction mixture is purified by silica gel column chromatography using hexane:ethyl acetate:dichloromethane=5:1:2 as a solvent to obtain the target compound.

Yellow solid, mp 177-5-177.8° C. (28.0 mg, 87%); IR (ATR) v=2996, 2920, 1582, 1404, 1438, 1377, 1150, 1024 cm$^{-1}$; $^1$H NMR (400 MHz, CDCl$_3$) δ 8.34 (d, J=8.0 Hz, 1H), 8.25 (d, J=8.0 Hz, 1H), 8.19 (s, 1H), 7.74-7.52 (m, 5H), 7.33 (d, J=9.6 Hz, 1H), 7.25 (s, 1H), 7.14 (d, J=8.4 Hz, 2H), 6.43 (s, 1H), 6.40 (s, 1H), 3.90 (s, 3H), 3.79 (s, 6H); $^{13}$C NMR (100 MHz, CDCl$_3$) δ 161.4, 160.5, 148.5, 143.2, 139.4, 138.1, 132.1, 130.3, 129.5, 127.7, 125.8, 124.6, 123.7, 123.6, 123.1, 122.5, 121.7, 119.2, 114.9, 104.1, 99.8, 92.4, 55.6, 55.5; HRMS (ESI) calcd for C$_{30}$H$_{25}$N$_2$O$_3$ 461.1860 ([M+H]$^+$). found 461.1859.

Example 41

6-(4-Methoxyphenyl)-9-(4-nitrophenyl)indolizino[3,2-c]quinoline

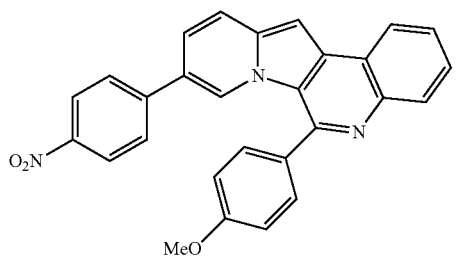 [SMILES: COc1ccc(-c2nc3ccccc3c3cc4ccc(-c5ccc([N+](=O)[O-])cc5)cn4c23)cc1]

The target compound is obtained in the same manner as Example 40, except that 4-nitrophenylboronic acid is used instead of 3,5-dimethoxyphenylboronic acid.

Orange solid, mp 256.0-256.6° C. (29.6 mg, 95%); IR (ATR) v=3920, 2851, 1594, 1560, 1439, 1380, 1334, 1171, 1024 cm$^{-1}$; $^1$H NMR (400 MHz, CDCl$_3$) δ 8.39 (d, J=8.0 Hz, 1H), 8.28 (d, J=8.4 Hz, 1H), 8.23 (d, J=8.8 Hz, 2H), 8.21 (s, 1H), 7.78-7.69 (m, 2H), 7.70-7.63 (m, 3H), 7.44 (d, J=8.8 Hz, 2H), 7.40-7.33 (m, 2H), 7.20 (d, J=8.4 Hz, 2H), 3.97 (s, 3H); $^{13}$C NMR (100 MHz, CDCl$_3$) δ 178.4, 160.9, 144.1, 132.6, 130.3, 129.7, 128.1, 127.9, 126.5, 126.1, 125.8, 124.51, 124.45, 123.7, 122.4, 122.0, 120.9, 119.9, 115.0, 93.3, 86.3, 55.9; HRMS (ESI) calcd for C$_{28}$H$_{20}$N$_3$O$_3$ 446.1499 ([M+H]$^+$). found 446.1495.

Example 42

9-(3,5-Dimethoxyphenyl)-6-(naphthalene-1-yl)indolizino[3,2-c]quinoline

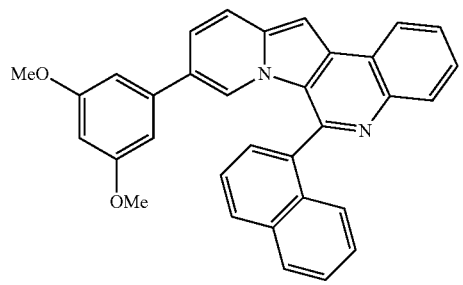 [SMILES: COc1cc(OC)cc(-c2ccc3cc4c5ccccc5nc(-c5cccc6ccccc56)c4n3c2)c1]

The target compound is obtained in the same manner as Example 40, except that the compound obtained from Example 27 is used instead of the compound obtained from Example 24.

Yellow solid, mp 177.5-177.8° C. (32.3 mg, 96%); IR (ATR) v=2991, 2958, 1591, 1439, 1376, 1199, 1153, 1067 cm$^{-1}$; $^1$H NMR (400 MHz, CDCl$_3$) δ 8.45 (d, J=7.6 Hz, 1H), 8.31 (d, J=8.0 Hz, 1H), 8.06 (d, J=8.4 Hz, 1H), 7.96 (d, J=8.4 Hz, 1H), 7.77 (d, J=6.4 Hz, 1H), 7.76-7.67 (m, 3H), 7.66 (d, J=9.2 Hz, 1H), 7.54-7.47 (m, 2H), 7.45 (d, J=8.4 Hz, 1H), 7.35 (s, 1H), 7.31 (t, J=7.6 Hz, 1H), 7.26 (d, J=8.0 Hz, 1H), 6.31 (s, 1H), 5.94 (d, J=2.0 Hz, 2H), 3.68 (s, 6H); $^{13}$C NMR (100 MHz, CDCl$_3$) δ 161.2, 147.3, 143.5, 139.2, 138.1, 137.0, 133.9, 131.9, 131.6, 129.8, 129.6, 128.6, 127.8, 127.5, 127.1, 126.8, 126.3, 126.1, 125.2, 124.13, 124.06, 123.74, 123.69, 122.7, 122.6, 119.0, 104.0, 99.9, 92.3, 55.5; HRMS (ESI) calcd for C$_{33}$H$_{25}$N$_2$O$_2$ 481.1911 ([M+H]$^+$). found 481.1909.

Example 43

9-(Furan-3-yl)-6-(naphthalene-1 yl)indolizino[3,2-c]quinoline

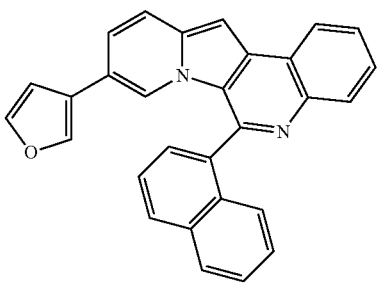 [SMILES: c1ccc2c(-c3nc4ccccc4c4cc5ccc(-c6ccoc6)cn5c34)cccc2c1]

The target compound is obtained in the same manner as Example 40, except that the compound obtained from Example 27 is used instead of the compound obtained from Example 24, and furan-3-yl-boronic acid is used instead of 3,5-dimethoxyphenylboronic acid.

Yellow solid, mp 91.3-92.0° C. (27.3 mg, 95%); IR (ATR) v=2920, 2850, 1561, 1436, 1315, 1251, 1016 cm$^{-1}$; $^1$H NMR (400 MHz, CDCl$_3$) δ 8.46 (d, J=6.8 Hz, 1H), 8.32 (d, J=8.0 Hz, 1H), 8.17 (d, J=8.4 Hz, 1H), 8.06 (d, J=8.4 Hz, 1H), 7.81-7.72 (m, 3H), 7.70 (t, J=8.0 Hz, 1H), 7.63 (d, J=9.2 Hz 1H), 7.53 (t, J=7.6 Hz, 1H), 7.44 (d, J=8.4 Hz, 1H), 7.35 (s, 1H), 7.31 (t, J=7.6 Hz, 1H), 7.28-7.26 (m, 1H), 7.26-7.24 (m, 1H), 7.17 (s, 1H), 7.11 (d, J=9.2 Hz, 1H), 5.64 (s, 1H); $^{13}$C NMR (100 MHz, CDCl$_3$) δ 144.0, 138.0, 131.7, 130.2, 129.6, 128.60, 128.55, 127.8, 127.7, 127.6, 127.3, 126.9, 126.3, 126.1, 125.2, 124.0, 123.7, 123.4, 123.0, 122.9, 122.6, 122.3, 119.3, 119.2, 117.4, 107.3, 92.6; HRMS (ESI) calcd for C$_{29}$H$_{19}$N$_2$O 411.1492 ([M+H]$^+$). found 411.1491.

Example 44

12-Bromo-6-(4-methoxyphenyl)indolizino[3,2-c] quinoline

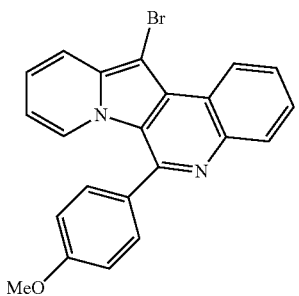 [SMILES: COc1ccc(-c2nc3ccccc3c3c(Br)c4ccccn4c23)cc1]

First, 0.1 mmol of the compound obtained from Example 7 and 0.1 mmol of N-bromosuccinimide are dissolved into 2 ml of dichloromethane and the reaction mixture is allowed to react at room temperature for 1 hour. After the completion of the reaction, the reaction mixture is concentrated under reduced pressure, and the concentrated reaction mixture is purified by silica gel column chromatography using hexane: ethyl acetate:dichloromethane=10:1:2 as a solvent to obtain the target compound.

Yellow solid, mp 221.6-221.9° C. (27.8 mg, 69%); IR (ATR) v=2921, 1609, 1493, 1438, 1356, 1248, 1024 cm$^{-1}$; $^1$H NMR (400 MHz, CDCl$_3$) δ 9.36 (d, J=7.6 Hz, 1H), 8.26 (d, J=8.0 Hz, 1H), 7.90 (d, J=7.2 Hz, 1H), 7.72 (d, J=8.4 Hz, 2H), 7.67 (t, J=8.0 Hz, 1H), 7.58 (d, J=8.4 Hz, 2H), 7.22-7.06 (m, 3H), 6.50 (t, J=6.8 Hz, 1H), 3.94 (s, 3H); $^{13}$C NMR (100 MHz, CDCl$_3$) δ 160.6, 148.2, 143.7, 136.1, 132.0, 130.1, 129.6, 128.0, 127.2, 126.9, 125.6, 124.5, 123.4, 122.1, 120.8, 117.7, 115.0, 110.7, 55.7; HRMS (ESI) calcd for C$_{22}$H$_{16}$BrN$_2$O 403.0441 ([M+H]$^+$). found 403.0435.

Test Examples

Test Example 1

Reaction Optimization Test

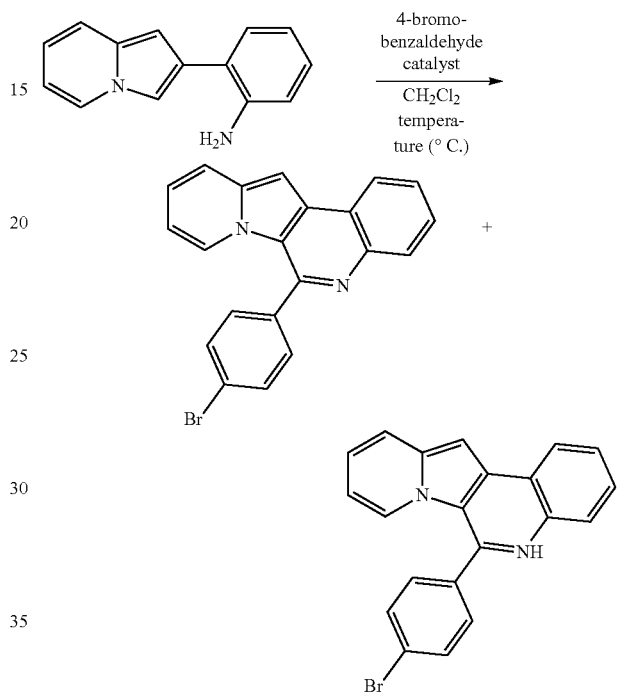

Reactivity depending on reaction temperature, catalyst and amount of catalyst is determined and the results are shown in the following Table 1.

TABLE 1

| | | | | Yield | |
| --- | --- | --- | --- | --- | --- |
| No. | Catalyst | Equivalent | Reaction Temperature | Target compound | Side product |
| 1 | PTSA | 0.1 | rt | 36 | 33 |
| 2 | PTSA | 0.1 | 60 | 46 | 25 |
| 3 | PPTS | 0.1 | rt | 18 | 62 |
| 4 | PPTS | 0.1 | 60 | 16 | 56 |
| 5 | InCl$_3$ | 0.1 | rt | 5 | 55 |
| 6 | InCl$_3$ | 0.1 | 60 | 27 | 34 |
| 7 | BiCl$_3$ | 0.1 | 60 | 10 | 41 |
| 8 | AlCl$_3$ | 0.1 | rt | 64 | 23 |
| 9 | AlCl$_3$ | 0.1 | 60 | 56 | 28 |
| 10 | FeCl$_3$ | 0.1 | rt | 41 | — |
| 11 | FeCl$_3$ | 0.1 | 40 | 71 | — |
| 12 | FeCl$_3$ | 0.1 | 60 | 72 | — |
| 13 | FeCl$_3$ | 0.2 | 60 | 83 | — |
| 14 | FeCl$_3$ | 0.3 | 60 | 77 | — |
| 15 | FeCl$_3$ | 0.5 | 60 | 41 | — |

As shown in Table 1, when using FeCl$_3$ as a catalyst, no side product is produced. In addition, it is possible to obtain a compound represented by Chemical Formula 1 with high yield, when a reaction temperature of 40-80° C., and 0.1-0.3 eq., particularly 0.2 eq. of a catalyst are used.

Test Example 2

Assay

Test Example 2.1

Cell Culture

Adipose-derived stem cells (ASC) and melanoma cells (B16 melanoma cells) are cultured in high-glucose Dulbecco's modified Eagle's medium (DMEM) with 10% fetal bovine serum (FBS) introduced thereto. Each type of cells is cultured in an incubator under the conditions of 37° C. and 5% $CO_2$.

Test Example 2.2

Proliferation/Viability Assay

Figure 3:
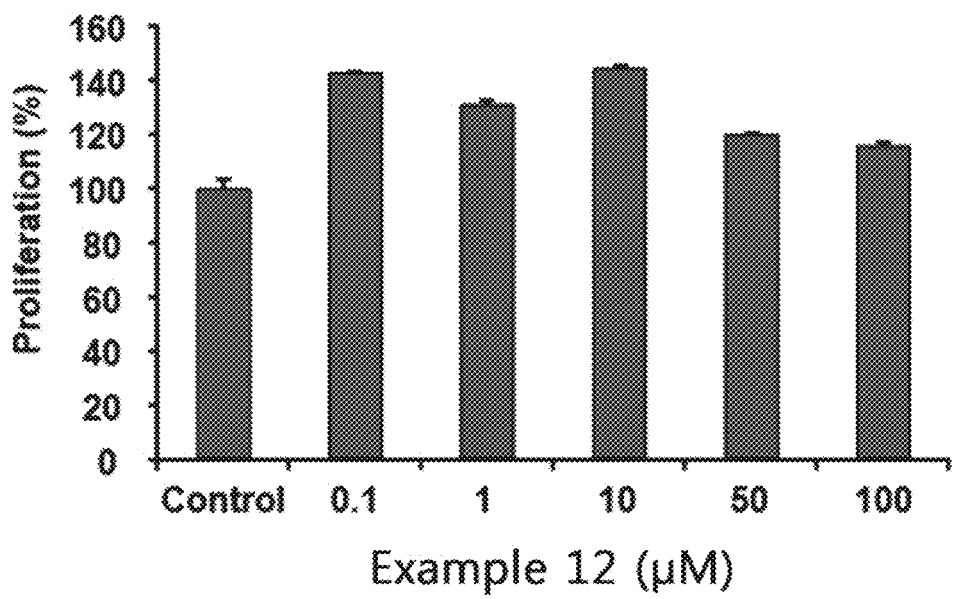
FIG. 3 is a graph illustrating the cytotoxicity of the compound according to Example 12.
Figure 4:
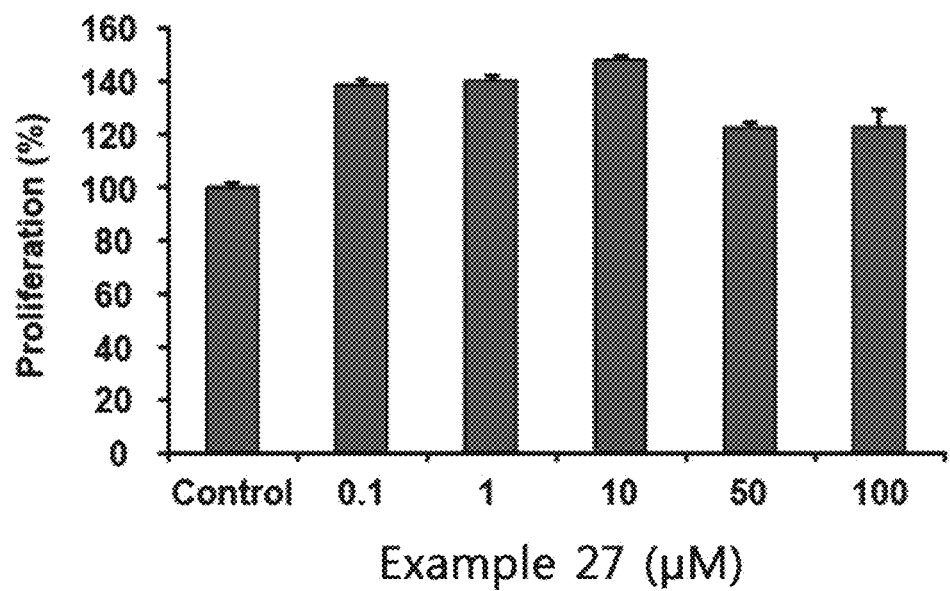
FIG. 4 is a graph illustrating the cytotoxicity of the compound according to Example 27.

Cell survivability and cytotoxicity are determined in a 96-well plate by MTT assay. Each type of cells is implanted into a 6-well plate in a number of $3 \times 10^4$/well (ASC) and $4 \times 10^4$/well and cultured for 24 hours. Then, media change into high-glucose DMEM is carried out for both ASC and B16 and cultured overnight. After starvation, the cells are treated with each of the compounds according to Examples at a different concentration (0.1, 1, 10, 50, 100 μM), and further incubated for 24 hours and 48 hours under the conditions of 37° C. and 5% $CO_2$. Then, MTT solution (5 mg/ml in PBS) is added to each well in an amount corresponding to 1/20 of the media volume, and incubation is carried out at 37° C. for 2 hours so that the cells are colored. After that, the supernatant is removed and dimethyl sulfoxide is added to carry out discoloration. The solution is determined by using an enzyme-linked immunosorbent assay (ELISA) reader at a wavelength of 595 nm. The results are shown in FIG. 2 to FIG. 4.

Figure 2:
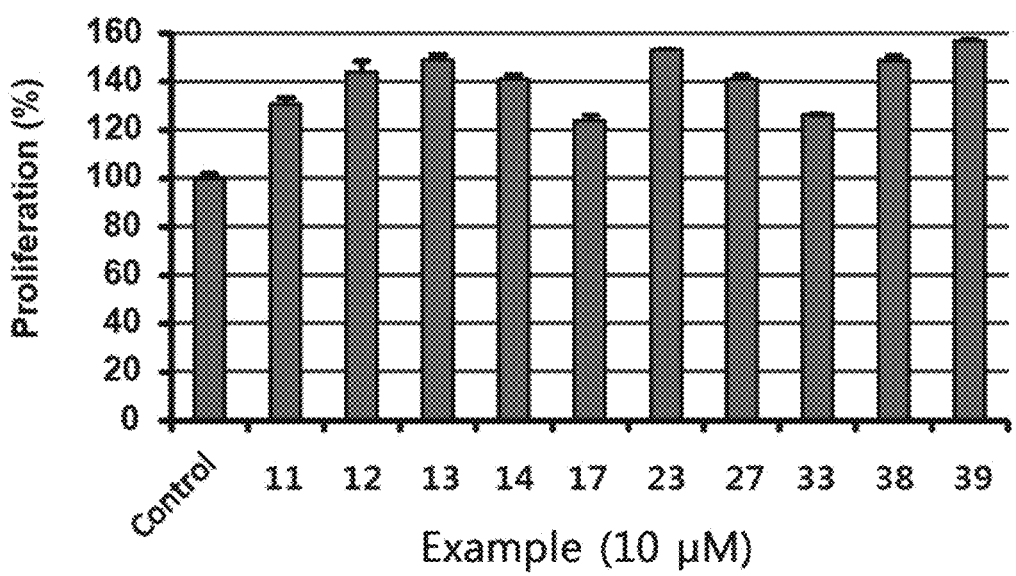
FIG. 2 is a graph illustrating the effect of stimulating proliferation of adipose-derived stem cells of the compound according to an embodiment of the present disclosure.

Referring to FIG. 2, it can be seen that when adipose-derived stem cells are treated with each compound according to Examples, proliferation of the cells increases, the compounds according to Examples 12, 14, 23 and 27 being highly effective. Particularly, as shown in FIG. 3 or FIG. 4, the compounds according to Examples 12 and 27 show no toxicity even at a high concentration of 100 μM and thus are expected to be useful as stem cell activators.

Test Example 2.3

Migration Assay

Adipose-derived stem cells are implanted into a 96-well plate in a number of $3 \times 10^4$/well and cultured for 24 hours. Then, media change into high-glucose DMEM is carried out and the cells are cultured overnight. After starvation, a mechanical wound is made and the cells are treated with each of the compounds according to Examples at a different concentration (0.1, 1, 10, 50 μM). Next, the cells are incubated for 24 hours and 48 hours under the conditions of 37° C. and 5% $CO_2$. Then, the Incucyte zoom (Essen Bioscience, USA) is photographed from the time point of treatment with each compound at an interval of 1 hour to analyze the migration of ASC.

Figure 5:
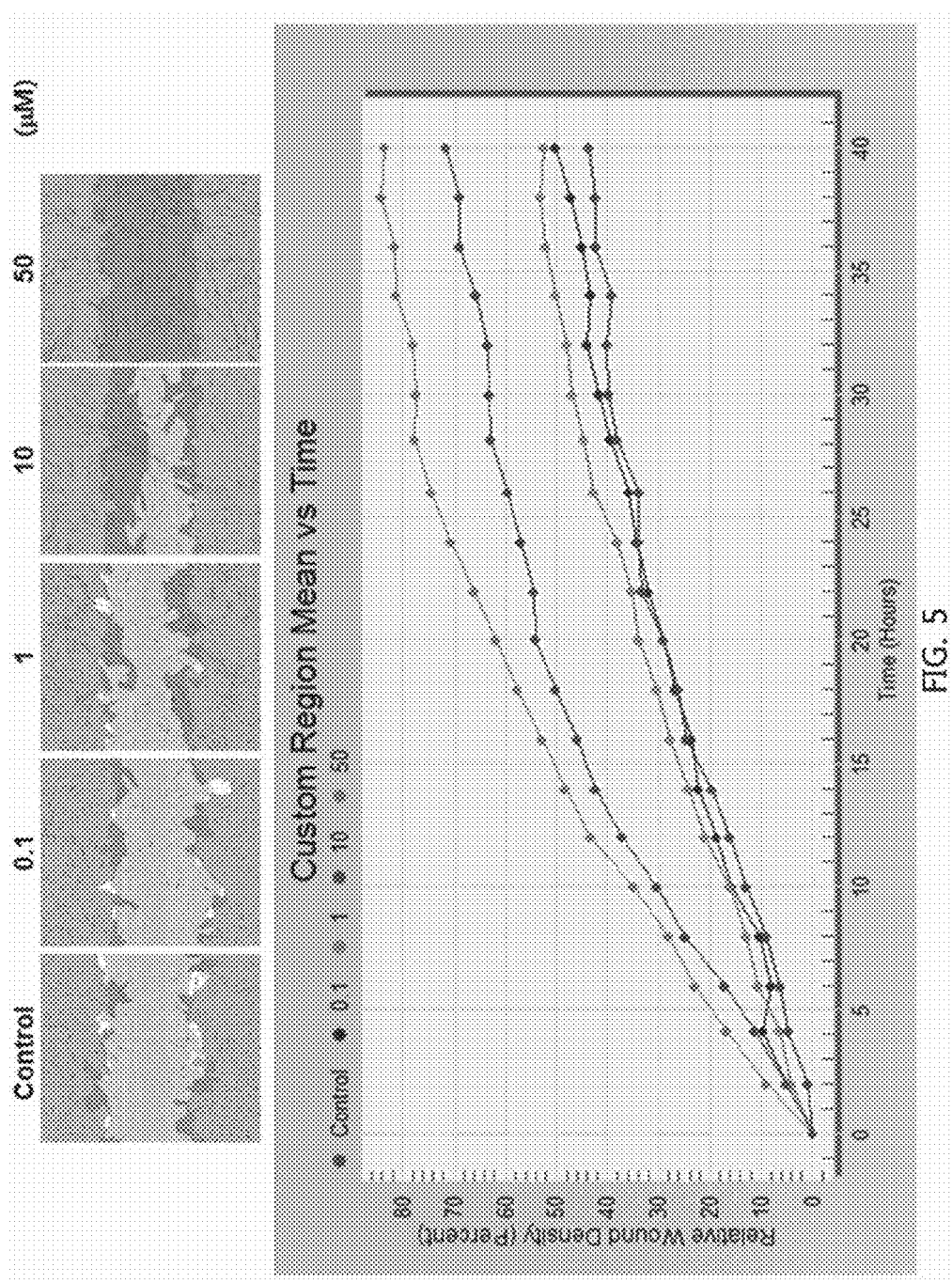
FIG. 5 is a graph illustrating the migration ability of adipose-derived stem cells when using the compound according to Example 12.
Figure 6:
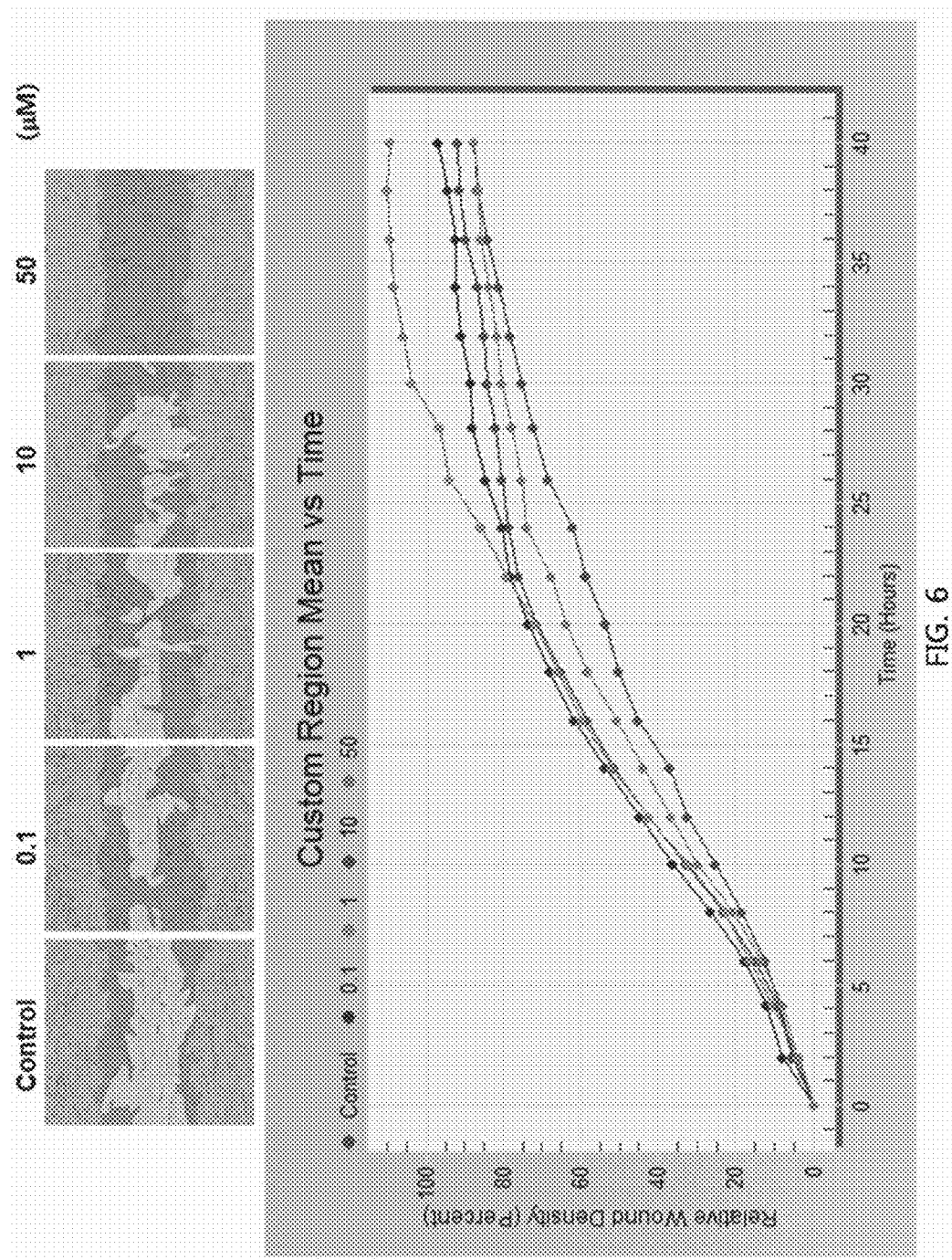
FIG. 6 is a graph illustrating the migration ability of adipose-derived stem cells when using the compound according to Example 27.

It can be seen from the migration assay of adipose-derived stem cells that each of the compounds according to Examples 12 and 27 has migration ability for adipose-derived stem cells, which is shown in FIG. 5 and FIG. 6. As can be seen from the foregoing, the compound according to the present disclosure stimulates proliferation and migration of adipose-derived stem cells, which suggests that the compound according to the present disclosure can be used as a composition for stimulating proliferation of stem cells and as a stem cell activator.

Test Example 3

Determination of Effect upon CFTR Chloride Ion Channel Activity

FRT cells expressing mutant trifunctional protein (TFP) specific to human cystic fibrosis conductance transmembrane regulator (CFTR) and iodide ions are cultured in the Coon's modified F-12 culture medium for 48 hours on a 96-well plate. Each well of the plate containing the cultured cells is washed three times with 200 μl of PBS buffer, and then 100 μl of PBS buffer is added to each well. The indolizino[3,2-c]quinoline derivative according to each Example is introduced to each well to a final concentration of 30 μM, followed by reaction for 10 minutes. After the completion of the reaction, the 96-well is mounted to a FLUOstar Omega microplate reader (BMG LABTECH) and 100 μl of NaI solution is added to each well. Then, YFP fluorescence reduced by the iodide ions introduced to the cells through CFTR is recorded at an interval of 0.4 seconds for 24 seconds in total, thereby evaluating the effect of each compound upon CFTR activity.

The effect of each indolizino[3,2-c]quinoline derivative upon CFTR chloride ion channel activity is calculated as an activity ratio based on the CFTR activity maximized by a well-known CFTR agonist, forskolin. The results are shown in the following Table 2.

TABLE 2

| Compound | Activity ratio (%) |
|---|---|
| Ex. 1 | 85 |
| Ex. 5 | 93 |
| Ex. 10 | 63 |
| Ex. 12 | 44 |
| Ex. 13 | 83 |
| Ex. 14 | 82 |
| Ex. 15 | 98 |
| Ex. 17 | 50 |
| Ex. 21 | 66 |
| Ex. 33 | 37 |
| Ex. 38 | 31 |

As shown in Table 2, the compounds according to the present disclosure strongly activate cystic fibrosis conductance transmembrane regulator. Particularly, it can be seen that the compounds according to Examples 1, 5, 10, 13, 14, 15 and 31 have a high activity ratio and stimulate water secretion in the bowel. Therefore, the compounds according to the present disclosure can be used as an agent for preventing or treating diseases caused by degradation of activity of cystic fibrosis conductance transmembrane regulator, such as cystic fibrosis, dry eye syndrome or constipation.

What is claimed is:

1. An indolizino[3,2-c]quinoline derivative represented by the following Chemical Formula 1 or pharmaceutically acceptable salt thereof:

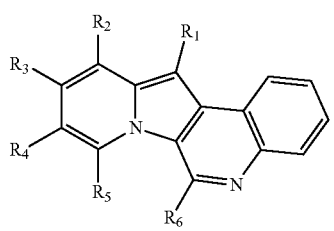

In Chemical Formula 1,
$R_1$, $R_2$, $R_3$, $R_4$ and $R_5$ are the same or different, and each independently represents H, F, Cl, Br, I, a C1-C6 alkyl, C1-C6 alkoxy, $COOR_7$, aryl and a heteroaryl;
$R_6$ is selected from a C1-C6 alkyl, aryl and a heteroaryl; and
$R_7$ is H or a C1-C6 alkyl, wherein any 1-3 carbon atoms of the aryl and heteroaryl are linked to a substituent that is the same or different and is independently selected from H, F, Cl, Br, I, nitro, a C1-C6 alkyl and C1-C6 alkoxy.

2. The indolizino[3,2-c]quinoline derivative represented by Chemical Formula 1 or pharmaceutically acceptable salt thereof according to claim 1, wherein the aryl is selected from phenyl, naphthyl, anthryl and biaryl.

3. The indolizino[3,2-c]quinoline derivative represented by Chemical Formula 1 or pharmaceutically acceptable salt thereof according to claim 1, wherein the heteroaryl is selected from pyridyl, pyrimidyl, thiophenyl, pyrollyl and furanyl.

4. The indolizino[3,2-c]quinoline derivative represented by Chemical Formula 1 or pharmaceutically acceptable salt thereof according to claim 1, wherein the C1-C6 alkyl is selected from the group consisting of methyl, ethyl, n-propyl, isopropyl, n-butyl, isobutyl, tert-butyl, n-propyl, isopropyl, n-hexyl and isohexyl.

5. The indolizino[3,2-c]quinoline derivative represented by Chemical Formula 1 or pharmaceutically acceptable salt thereof according to claim 1, wherein the compound represented by Chemical Formula 1 is at least one selected from the group consisting of the following Chemical Formula 6 through Chemical Formula 49:

[Chemical Formula 6]

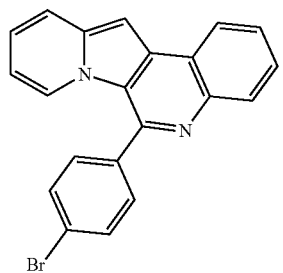

[Chemical Formula 7]

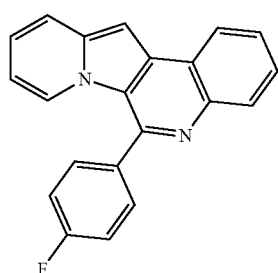

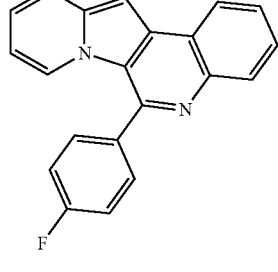
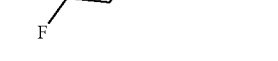

[Chemical Formula 8]

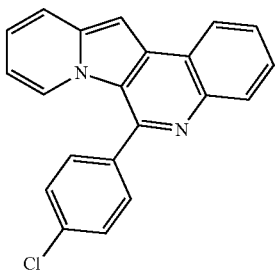

[Chemical Formula 9]

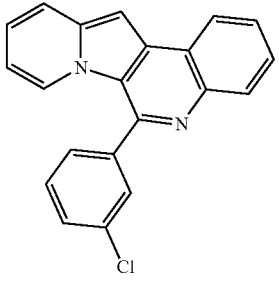

[Chemical Formula 10]

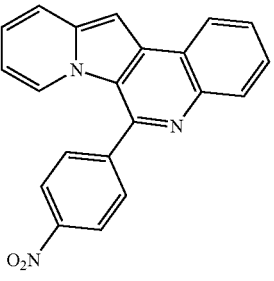

[Chemical Formula 11]

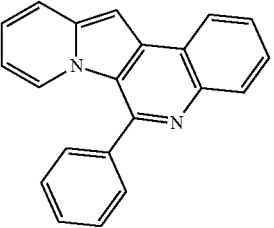

[Chemical Formula 12]

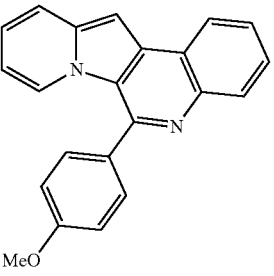

[Chemical Formula 13]

[Chemical Formula 14]
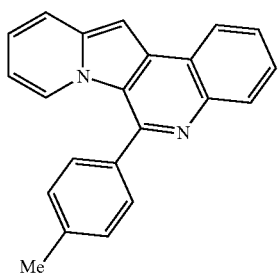
[Chemical Formula 15]
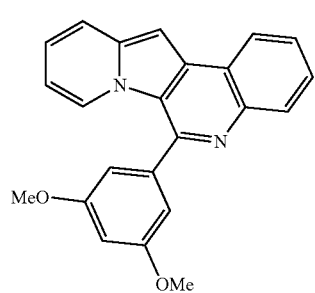
[Chemical Formula 16]
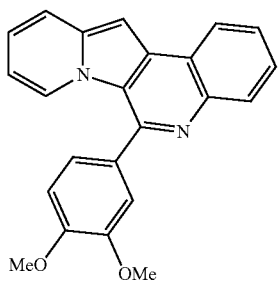
[Chemical Formula 17]
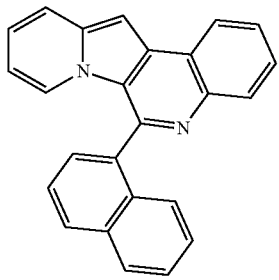
[Chemical Formula 18]
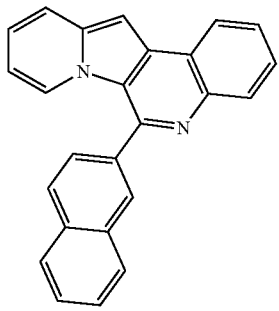
[Chemical Formula 19]
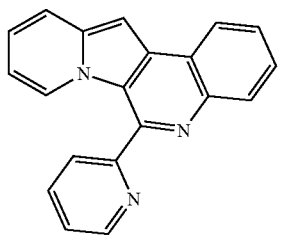
[Chemical Formula 20]
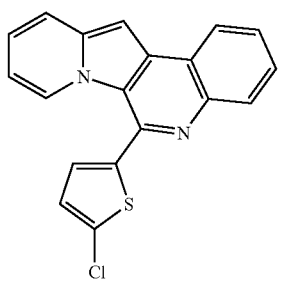
[Chemical Formula 21]
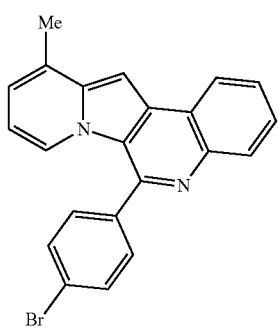
[Chemical Formula 22]
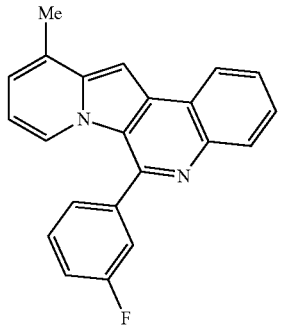
[Chemical Formula 23]
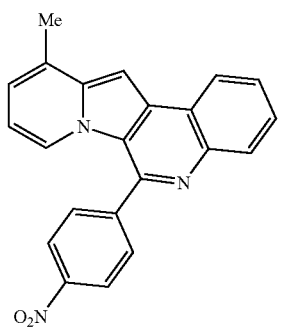

[Chemical Formula 24]
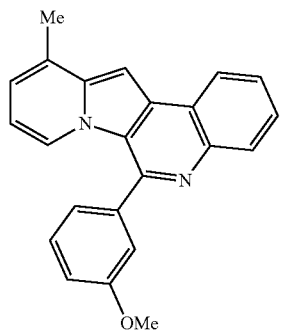
[Chemical Formula 25]
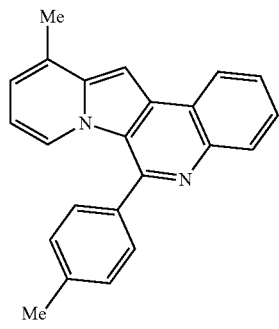
[Chemical Formula 26]
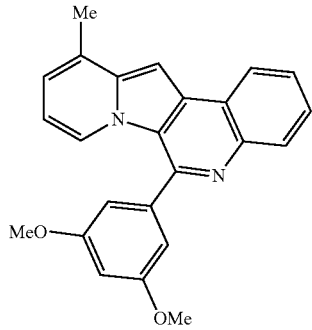
[Chemical Formula 27]
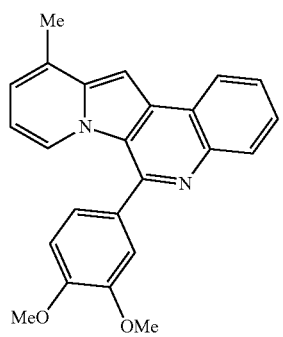
[Chemical Formula 28]
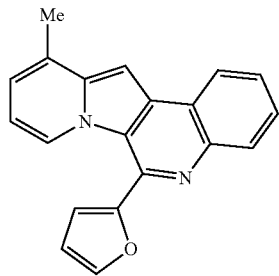
[Chemical Formula 29]
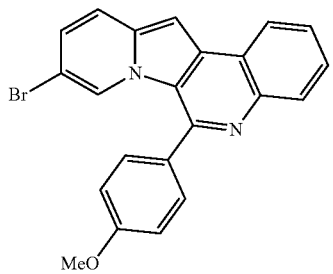
[Chemical Formula 30]
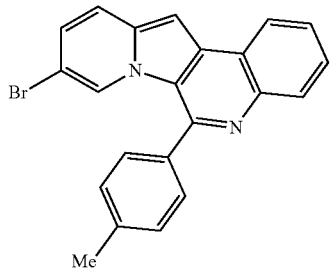
[Chemical Formula 31]
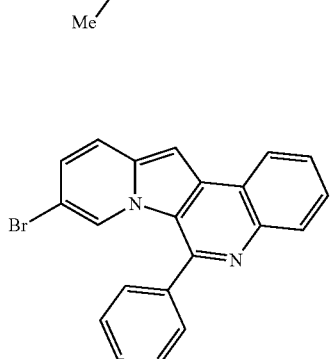
[Chemical Formula 32]
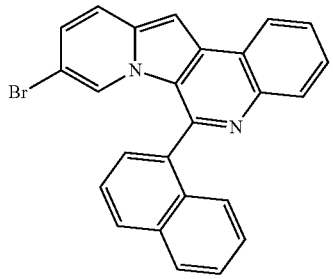
[Chemical Formula 33]
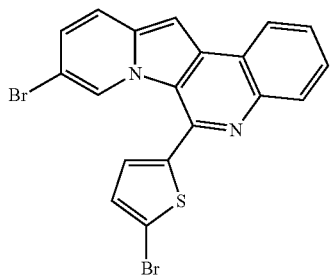

[Chemical Formula 34]
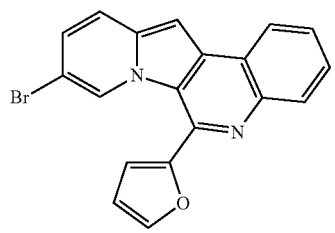
[Chemical Formula 35]
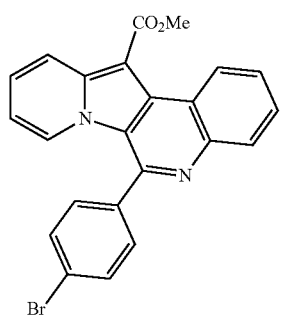
[Chemical Formula 36]
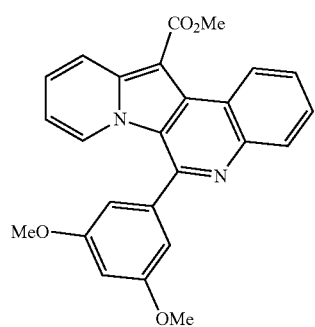
[Chemical Formula 37]
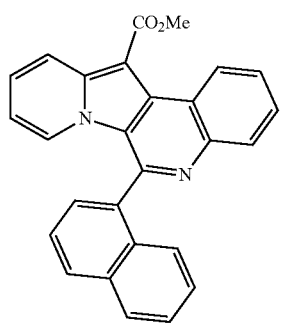
[Chemical Formula 38]
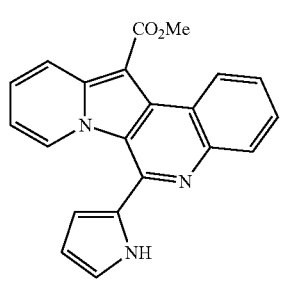
[Chemical Formula 39]
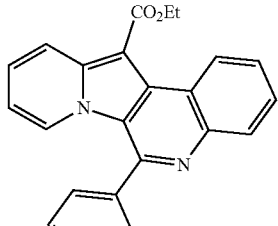
[Chemical Formula 40]
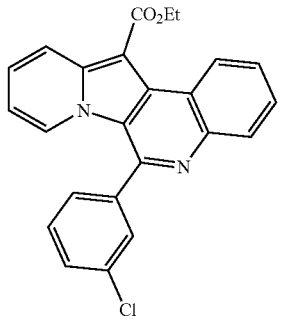
[Chemical Formula 41]
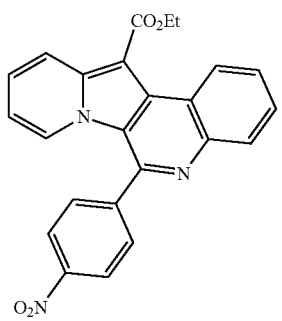
[Chemical Formula 42]
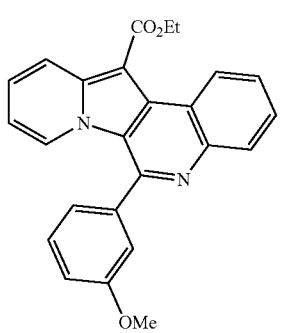
[Chemical Formula 43]
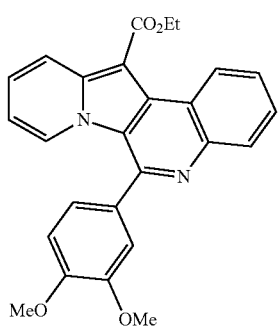

-continued

[Chemical Formula 44]
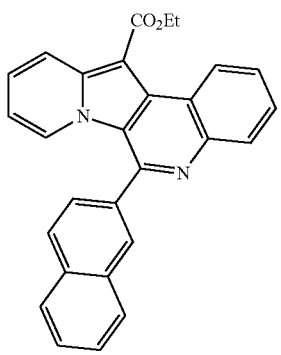

[Chemical Formula 45]
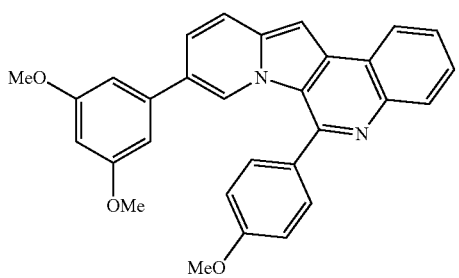

[Chemical Formula 46]
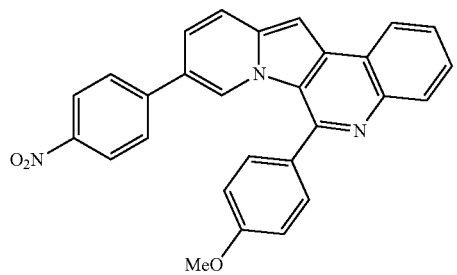

[Chemical Formula 47]
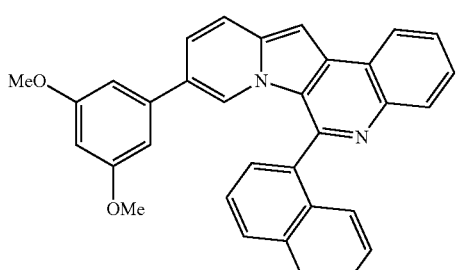

[Chemical Formula 48]
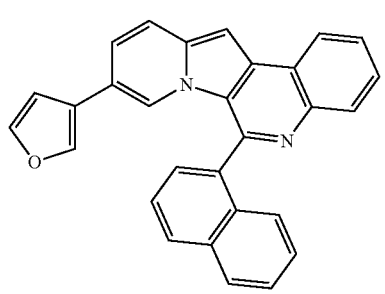

-continued

[Chemical Formula 49]
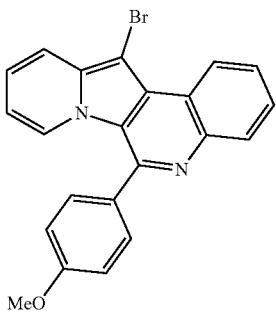

6. A method for preparing an indolizino[3,2-c]quinoline derivative represented by the following Chemical Formula 1 by reacting a compound represented by the following Chemical Formula 2 with an aldehyde in the presence of a catalyst:

[Chemical Formula 1]
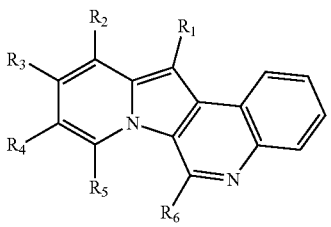

[Chemical Formula 2]
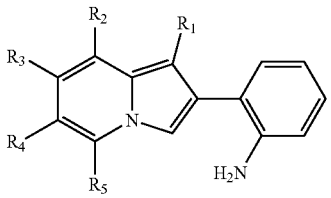

In Chemical Formula 1 or Chemical Formula 2, $R_1$, $R_2$, $R_3$, $R_4$ and $R_5$ are the same or different, and each independently represents H, F, Cl, Br, I, a C1-C6 alkyl, C1-C6 alkoxy, COOR$_7$, aryl and a heteroaryl;

$R_6$ is selected from a C1-C6 alkyl, aryl and a heteroaryl; and $R_7$ is H or a C1-C6 alkyl, wherein any 1-3 carbon atoms of the aryl and heteroaryl are linked to a substituent that is the same or different and is independently selected from H, F, Cl, Br, I, nitro, a C1-C6 alkyl and C1-C6 alkoxy.

7. The method for preparing an indolizino[3,2-c]quinoline derivative according to claim 6, wherein the catalyst is any one selected from FeCl$_3$, AlCl$_3$, BiCl$_3$, InCl$_3$, PTSA (p-toluenesulfonic acid) and PPTS (pyridinium p-toluenesulfonic acid).

8. The method for preparing an indolizino[3,2-c]quinoline derivative according to claim 6, wherein the reaction is carried out in a solvent selected from methylene chloride, N,N-dimethytformamide and tetrahydrofuran at 20-80° C.

9. The method for preparing an indolizino[3,2-c]quinoline derivative according to claim 6, wherein the compound represented by the above Chemical Formula 2 is obtained by reducing a compound represented by the following Chemical Formula 3:

[Chemical Formula 2]

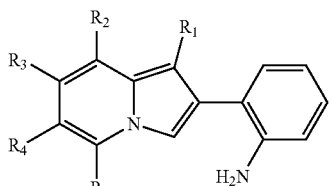

[Chemical Formula 3]

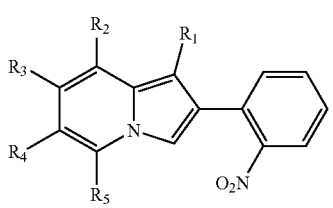

10. The method for preparing an indolizino[3,2-c]quinoline derivative according to claim 9, wherein the compound represented by the above Chemical Formula 3 is obtained by reacting a compound represented by the following Chemical Formula 4 with a compound represented by the following Chemical Formula 5:

[Chemical Formula 4]

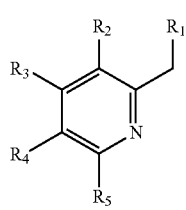

[Chemical Formula 5]

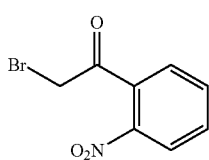

11. An agonist of cystic fibrosis conductance transmembrane regulator (CFTR), comprising the indolizino[3,2-c]quinoline derivative represented by the following Chemical Formula 1 or pharmaceutically acceptable salt thereof as an active ingredient:

[Chemical Formula 1]

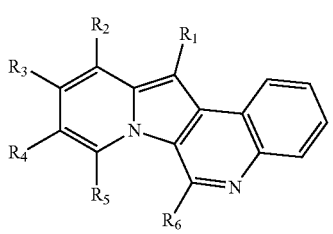

In Chemical Formula 1,
$R_1$, $R_2$, $R_3$, $R_4$ and $R_5$ are the same or different, and each independently represents H, F, Cl, Br, I, a C1-C6 alkyl, C1-C6 alkoxy, COOR$_7$, aryl and a heteroaryl;
$R_6$ is selected from a C1-C6 alkyl, aryl and a heteroaryl; and
$R_7$ is H or a C1-C6 alkyl, wherein any 1-3 carbon atoms of the aryl and heteroaryl are linked to a substituent that is the same or different and is independently selected from H, F, Cl, Br, I, nitro, a C1-C6 alkyl and C1-C6 alkoxy.

12. A pharmaceutical composition for treating diseases caused by degradation of activity of cystic fibrosis conductance transmembrane regulator, comprising the indolizino[3,2-c]quinoline derivative represented by the following Chemical Formula 1 or pharmaceutically acceptable salt thereof as an active ingredient:

[Chemical Formula 1]

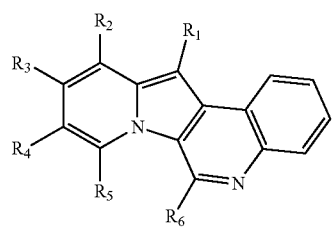

In Chemical Formula 1,
$R_1$, $R_2$, $R_3$, $R_4$ and $R_5$ are the same or different, and each independently represents H, F, Cl, Br, I, a C1-C6 alkyl, C1-C6 alkoxy, COOR$_7$, aryl and a heteroaryl;
$R_6$ is selected from a C1-C6 alkyl, aryl and a heteroaryl; and
$R_7$ is H or a C1-C6 alkyl, wherein any 1-3 carbon atoms of the aryl and heteroaryl are linked to a substituent that is the same or different and is independently selected from H, F, Cl, Br, I, nitro, a C1-C6 alkyl and C1-C6 alkoxy.

13. The pharmaceutical composition for treating diseases caused by degradation of activity of cystic fibrosis conductance transmembrane regulator according to claim 12, wherein the disease caused by degradation of activity of cystic fibrosis conductance transmembrane regulator is at least one selected from cystic fibrosis and dry eye syndrome.

14. A pharmaceutical composition for stimulating stem cell proliferation, comprising the indolizino[3,2-c]quinoline derivative represented by the following Chemical Formula 1 or pharmaceutically acceptable salt thereof as an active ingredient:

[Chemical Formula 1]

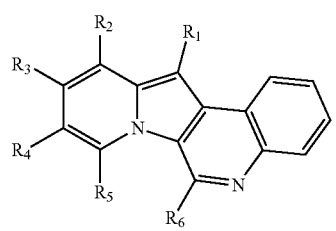

In Chemical Formula 1,
$R_1$, $R_2$, $R_3$, $R_4$ and $R_5$ are the same or different, and each independently represents H, F, Cl, Br, I, a C1-C6 alkyl, C1-C6 alkoxy, COOR$_7$, aryl and a heteroaryl;
$R_6$ is selected from a C1-C6 alkyl, aryl and a heteroaryl; and
$R_7$ is H or a C1-C6 alkyl, wherein any 1-3 carbon atoms of the aryl and heteroaryl are linked to a substituent that is the same or different and is independently selected from H, F, Cl, Br, I, nitro, a C1-C6 alkyl and C1-C6 alkoxy.

15. The pharmaceutical composition for stimulating stem cell proliferation according to claim 14, wherein the stem cell is any one selected from adipose-derived stem cells, neural stem cells, mesenchymal stem cells and adult stem cells.

* * * * *